US012799110B2

(12) United States Patent
Galan et al.

(10) Patent No.: US 12,799,110 B2
(45) Date of Patent: Nov. 17, 2026

(54) COMPOUNDS COMPRISING A HETERO-FLUORENE GROUP

(71) Applicant: Novaled GmbH, Dresden (DE)

(72) Inventors: Elena Galan, Dresden (DE); Jens Wutke, Dresden (DE); Lidia Marin, Dresden (DE)

(73) Assignee: Novaled GmbH, Dresden (DE)

(*) Notice: Subject to any disclaimer, the term of this patent is extended or adjusted under 35 U.S.C. 154(b) by 888 days.

(21) Appl. No.: 17/607,806

(22) PCT Filed: Apr. 8, 2020

(86) PCT No.: PCT/EP2020/060033

§ 371 (c)(1),
(2) Date: Oct. 29, 2021

(87) PCT Pub. No.: WO2020/221570

PCT Pub. Date: Nov. 5, 2020

(65) Prior Publication Data

US 2022/0231234 A1 Jul. 21, 2022

(30) Foreign Application Priority Data

Apr. 29, 2019 (EP) .................................... 19171659

(51) Int. Cl.
*C07D 471/00* (2006.01)
*C07D 401/10* (2006.01)
(Continued)

(52) U.S. Cl.
CPC ......... *C07D 471/00* (2013.01); *C07D 401/10* (2013.01); *C07D 405/14* (2013.01);
(Continued)

(58) Field of Classification Search
CPC ... C07D 401/10; C07D 405/14; H10K 85/654
See application file for complete search history.

(56) References Cited

U.S. PATENT DOCUMENTS

2012/0211082 A1* 8/2012 Akiyama .......... C07F 9/655372
977/734
2015/0060808 A1* 3/2015 Kim ..................... H10K 85/654
546/15

(Continued)

FOREIGN PATENT DOCUMENTS

CN 105440024 A 3/2016
CN 106910831 A 6/2017

(Continued)

OTHER PUBLICATIONS

PCT International Preliminary Report on Patentability for PCT Application No. PCT/EP2020/060033 mailed Nov. 2, 2021 (7 pages).

(Continued)

*Primary Examiner* — Alexander C Kollias
(74) *Attorney, Agent, or Firm* — Eversheds Sutherland (US) LLP

(57) ABSTRACT

The present invention relates to a compound, and to an organic semiconductor layer comprising this compound, suitable for use as an organic semiconductor layer for electronic devices, and a method of manufacturing the same, wherein the compound comprises a hetero-fluorene group and is represented by formula 1.

(Continued)

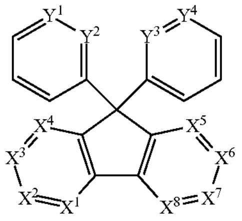

(I)

10 Claims, 2 Drawing Sheets

(51) Int. Cl.

| | |
|---|---|
| ***C07D 405/14*** | (2006.01) |
| ***C09K 11/06*** | (2006.01) |
| ***H10K 85/60*** | (2023.01) |
| *H10K 50/16* | (2023.01) |
| *H10K 101/30* | (2023.01) |

(52) U.S. Cl.

CPC ............ *C09K 11/06* (2013.01); *H10K 85/654* (2023.02); *H10K 85/6572* (2023.02); *H10K 85/6574* (2023.02); *C09K 2211/1018* (2013.01); *H10K 50/16* (2023.02); *H10K 2101/30* (2023.02)

(56) References Cited

U.S. PATENT DOCUMENTS

| | | | | |
|---|---|---|---|---|
| 2015/0129861 | A1* | 5/2015 | Hamano .............. | H10K 85/657 252/500 |
| 2017/0179395 | A1* | 6/2017 | Kim ................... | H10K 85/6574 |
| 2017/0179408 | A1* | 6/2017 | Sim ...................... | H10K 85/654 |
| 2017/0186967 | A1* | 6/2017 | Hayashi ............... | H10K 85/624 |
| 2018/0114922 | A1* | 4/2018 | Chen .................... | C09K 11/025 |
| 2019/0292181 | A1* | 9/2019 | Yang .................... | C07D 401/14 |

FOREIGN PATENT DOCUMENTS

| | | | |
|---|---|---|---|
| CN | 107011184 | A | 8/2017 |
| CN | 107112427 | A | 8/2017 |
| CN | 106349251 | B | 7/2018 |
| KR | 20190109881 | A | 9/2019 |

OTHER PUBLICATIONS

Decision of Rejection issued in China application No. 202080032062.4, dated May 22, 2024 (25 pages).

Communication pursuant to Article 94(3) EPC issued in European application No. 19171659.6, dated Oct. 25, 2022, 5 pages.

PCT, "International Search Report & Written Opinion" Application No. PCT/EP2020/060033, mailed May 8, 2020; 8 pages.

* cited by examiner

COMPOUNDS COMPRISING A HETERO-FLUORENE GROUP

CROSS REFERENCE TO RELATED APPLICATIONS

This application is a U.S. national stage application of PCT/EP2020/060033, filed Apr. 8, 2020, which claims priority to European Application No. 19171659.6, filed Apr. 29, 2019. The content of these applications is incorporated herein by reference.

TECHNICAL FIELD

The present invention relates to a compound comprising a hetero-fluorene group, in particular to an organic semiconductor layer comprising the compound, suitable for use as an organic semiconductor layer for electronic devices, and a method of manufacturing the same.

BACKGROUND ART

Organic electronic devices, such as organic light-emitting diodes OLEDs, which are self-emitting devices, have a wide viewing angle, excellent contrast, quick response, high brightness, excellent operating voltage characteristics, and color reproduction. A typical OLED comprises an anode, a hole transport layer HTL, an emission layer EML, an electron transport layer ETL, and a cathode, which are sequentially stacked on a substrate. In this regard, the HTL, the EML, and the ETL are thin films formed from organic compounds.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency and/or a long lifetime.

Performance of an organic light emitting diode may be affected by characteristics of the organic semiconductor layer, and among them, may be affected by characteristics of an organic material of the organic semiconductor layer.

Particularly, development of an organic semiconductor layer being capable of increasing electron mobility and simultaneously increasing electrochemical stability is needed so that the organic electronic device, such as an organic light emitting diode, may be applied to a large-size flat panel display.

Further, development of an organic semiconductor layer being capable to have an extended life span at higher current density and thereby at higher brightness is needed.

There remains a need to improve performance of organic compounds for use as semiconductor materials, organic semiconductor layers, as well as organic electronic devices thereof, in particular to achieve increased lifetime through improving the characteristics of the compounds comprised therein.

DISCLOSURE

An aspect of the present invention provides a compound having the formula 1:

(1)

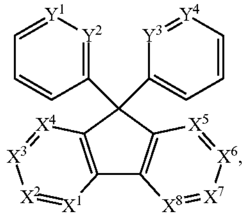

wherein $X^1$, $X^2$, $X^3$, $X^3$, $X^4$, $X^5$, $X^6$, $X^7$ and $X^8$ are independently selected from C—H, N, C—$R^1$, wherein $R^1$ are independently selected from CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, alkenyl, formula 2, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

wherein at least one of $X^1$ to $X^8$ but not more than four of $X^1$ to $X^8$ are N, and wherein at least one of $R^1$ but not more than three of $R^1$ are formula 2:

$$*—L—[G]_n, \quad (2)$$

wherein L is a direct bond, phenylene or biphenylene, substituted or unsubstituted $C_6$ to $C_{18}$ arylene, substituted or unsubstituted $C_3$ to $C_{20}$ heteroarylene, or $C_6$ to $C_{40}$ alkenyl, wherein the substituents of the substituted $C_6$ to $C_{18}$ arylene and substituted $C_3$ to $C_{20}$ heteroarylene are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S;

wherein G is independently selected from unsubstituted or substituted $C_6$ to $C_{40}$ aryl or $C_3$ to $C_{42}$ heteroaryl, $C_6$ to $C_{40}$ alkenyl, CN, $PY(R^2)_2$ with Y being O or S wherein the substituents of the substituted $C_6$ to $C_{18}$ aryl and of the substituted $C_3$ to $C_{20}$ heteroaryl are independently selected from H, CN, F, deuterium, $C_6$ to $C_{18}$ aryl, $C_3$ to $C_{20}$ heteroaryl, $C_1$ to $C_{16}$ alkyl, $C_1$ to $C_{16}$ alkoxy, nitrile, and $PY(R^2)_2$ with Y being O or S;

n=0, 1, 2 or 3;

$Y^1$, $Y^2$, $Y^3$ and $Y^4$ are C—$R^3$, wherein $R^3$ is independently selected from H, CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, $C_6$ to $C_{40}$ alkenyl, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

or $Y^2$ and $Y^3$ are C and connected via a single bond or bridged by formula 3,

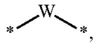

(3)

wherein W is $CH_2$, C—$(CH_3)_2$, N—H, N—$R^4$, O or S, and $Y^1$ and $Y^4$ are C—H, wherein $R^4$ is selected from $C_1$ to $C_6$ alkyl, substituted or unsubstituted $C_6$ to $C_{18}$ aryl, substituted or unsubstituted $C_2$ to $C_{20}$ heteroaryl, wherein the substituents of the substituted $C_6$ to $C_{18}$ aryl and substituted $C_3$ to $C_{20}$ heteroaryl are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S; or $Y^1$, $Y^2$ and $Y^3$ are C, wherein $Y^1$ and $Y^2$ are part of an annelated benzene ring and the annelated benzene ring is connected via a single bond to $Y^3$;

and wherein the hetero atom is selected from N, O or S;

and wherein $R^2$ are the same or different and independently selected from the group consisting of $C_1$ to $C_{16}$ alkyl, $C_1$ to $C_{16}$ alkoxy, $C_6$ to $C_{26}$ alkenyl, $C_6$ to $C_{18}$ aryl and $C_3$ to $C_{25}$ heteroaryl.

According to one embodiment, the compound is represented by formula 1:

(1)

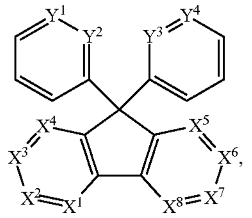

wherein $X^1$, $X^2$, $X^3$, $X^3$, $X^4$, $X^5$, $X^6$, $X^7$ and $X^8$ are independently selected from C—H, N, C—$R^1$, wherein $R^1$ are independently selected from CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, alkenyl, formula 2, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

wherein at least one of $X^1$ to $X^8$ but not more than four of $X^1$ to $X^8$ are N, at least one to three are C—$R^1$, preferably one is C—$R^1$, and wherein at least one of $R^1$ but not more than three of $R^1$ are formula 2:

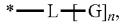

(2)

wherein L is a direct bond, phenylene or biphenylene, substituted or unsubstituted $C_6$ to $C_{18}$ arylene, substituted or unsubstituted $C_3$ to $C_{20}$ heteroarylene, or $C_6$ to $C_{40}$ alkenyl, wherein the substituents of the substituted $C_6$ to $C_{18}$ arylene and substituted $C_3$ to $C_{20}$ heteroarylene are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S;

wherein G is independently selected from unsubstituted or substituted $C_6$ to $C_{40}$ aryl or $C_3$ to $C_{42}$ heteroaryl, $C_6$ to $C_{40}$ alkenyl, CN, $PY(R^2)_2$ with Y being O or S wherein the substituents of the substituted $C_6$ to $C_{18}$ aryl and of the substituted $C_3$ to $C_{20}$ heteroaryl are independently selected from H, CN, F, deuterium, $C_6$ to $C_{18}$ aryl, $C_3$ to $C_{20}$ heteroaryl, $C_1$ to $C_{16}$ alkyl, $C_1$ to $C_{16}$ alkoxy, nitrile, and $PY(R^2)_2$ with Y being O or S;

n=0, 1, 2 or 3;

$Y^1$, $Y^2$, $Y^3$ and $Y^4$ are C—$R^3$, wherein $R^3$ is independently selected from H, CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, $C_6$ to $C_{40}$ alkenyl, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

or $Y^2$ and $Y^3$ are C and connected via a single bond or bridged by formula 3, (3)

wherein W is $CH_2$, C—$(CH_3)_2$, N—H, N—$R^4$, O or S, and $Y^1$ and $Y^4$ are C—H, wherein $R^4$ is selected from $C_1$ to $C_6$ alkyl, substituted or unsubstituted $C_6$ to $C_{18}$ aryl, substituted or unsubstituted $C_2$ to $C_{20}$ heteroaryl, wherein the substituents of the substituted $C_6$ to $C_{18}$ aryl and substituted $C_3$ to $C_{20}$ heteroaryl are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S; or $Y^1$, $Y^2$ and $Y^3$ are C, wherein $Y^1$ and $Y^2$ are part of an annelated benzene ring and the annelated benzene ring is connected via a single bond to $Y^3$;

and wherein the hetero atom is selected from N, O or S;

and wherein $R^2$ are the same or different and independently selected from the group consisting of $C_1$ to $C_{16}$ alkyl, $C_1$ to $C_{16}$ alkoxy, $C_6$ to $C_{26}$ alkenyl, $C_6$ to $C_{18}$ aryl and $C_3$ to $C_{25}$ heteroaryl; and with the provision one of $X^1$, $X^2$, $X^3$, $X^3$, $X^4$, $X^5$, $X^6$, $X^7$ and $X^8$ are selected N, if $X^8$ is selected N or if $X^1$ is selected N, then formula 2 comprises at least one hetero atom selected from N, O or S, preferably N; and with the provision two of $X^1$, $X^2$, $X^3$, $X^3$, $X^4$, $X^5$, $X^6$, $X^7$ and $X^8$ are selected N, then $X^3$ and $X^7$ are N, or $X^3$ and $X^5$ are N.

According to one embodiment, the compound is represented by formula 1:

(1)

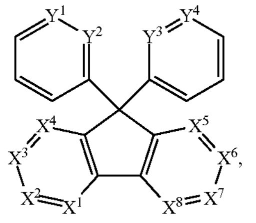

wherein $X^1$, $X^2$, $X^3$, $X^3$, $X^4$, $X^5$, $X^6$, $X^7$ and $X^8$ are independently selected from C—H, N, C—$R^1$, wherein $R^1$ are independently selected from CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, alkenyl, formula 2, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

wherein at least one of $X^1$ to $X^8$ but not more than four of $X^1$ to $X^8$ are N, at least one to three are C—$R^1$, preferably one is C—$R^1$, and wherein at least one of $R^1$ but not more than three of $R^1$ are formula 2:

$$*-L-[G]_n, \quad (2)$$

with the provision regarding $X^1$ to $X^8$:

if one selected N, namely $X^1$ or $X^8$, then formula 2 comprises at least one hetero atom selected from N, O or S, preferably N; and/or if two selected N, then $X^3$ and $X^7$, or $X^3$ and $X^5$ are N;

wherein L is a direct bond, phenylene or biphenylene, substituted or unsubstituted $C_6$ to $C_{18}$ arylene, substituted or unsubstituted $C_3$ to $C_{20}$ heteroarylene, or $C_6$ to $C_{40}$ alkenyl, wherein the substituents of the substituted $C_6$ to $C_{18}$ arylene and substituted $C_3$ to $C_{20}$ heteroarylene are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S;

wherein G is independently selected from unsubstituted or substituted $C_6$ to $C_{40}$ aryl or $C_3$ to $C_{42}$ heteroaryl, $C_6$ to $C_{40}$ alkenyl, CN, $PY(R^2)_2$ with Y being O or S wherein the substituents of the substituted $C_6$ to $C_{18}$ aryl and of the substituted $C_3$ to $C_{20}$ heteroaryl are independently selected from H, CN, F, deuterium, $C_6$ to $C_{18}$ aryl, $C_3$ to $C_{20}$ heteroaryl, $C_1$ to $C_{16}$ alkyl, $C_1$ to $C_{16}$ alkoxy, nitrile, and $PY(R^2)_2$ with Y being O or S;

n=0, 1, 2 or 3;

$Y^1$, $Y^2Y^3$ and $Y^4$ are C—$R^3$, wherein $R^3$ is independently selected from H, CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, $C_6$ to $C_{40}$ alkenyl, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

or $Y^2$ and $Y^3$ are C and connected via a single bond or bridged by formula 3, (3)

wherein W is $CH_2$, C—$(CH_3)_2$, N—H, N—$R^4$, O or S, and $Y^1$ and $Y^4$ are C—H, wherein $R^4$ is selected from $C_1$ to $C_6$ alkyl, substituted or unsubstituted $C_6$ to $C_{18}$ aryl, substituted or unsubstituted $C_2$ to $C_{20}$ heteroaryl, wherein the substituents of the substituted $C_6$ to $C_{18}$ aryl and substituted $C_3$ to $C_{20}$ heteroaryl are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S; or $Y^1$, $Y^2$ and $Y^3$ are C, wherein $Y^1$ and $Y^2$ are part of an annelated benzene ring and the annelated benzene ring is connected via a single bond to $Y^3$; and wherein the hetero atom is selected from N, O or S; and wherein $R^2$ are the same or different and independently selected from the group consisting of $C_1$ to $C_{16}$ alkyl, $C_1$ to $C_{16}$ alkoxy, $C_6$ to $C_{26}$ alkenyl, $C_6$ to $C_{18}$ aryl and $C_3$ to $C_{25}$ heteroaryl.

According to one embodiment of formula 1, wherein in formula 1:

one of $X^1$, $X^2$, $X^3$, $X^3$, $X^4$, $X^5$, $X^6$, $X^7$ and $X^8$ are selected N and at least one are C—$R^1$ but not more than three are C—$R^1$, then if $X^1$ is selected N or if $X^8$ is selected N, then at least one of $R^1$ but not more than three of $R^1$, preferably one of $R^1$, are formula 2 comprising at least one hetero atom selected from N, O or S; or two of $X^1$, $X^2$, $X^3$, $X^3$, $X^4$, $X^5$, $X^6$, $X^7$ and $X^8$ are selected N and at least one is C—$R^1$ but not more than three are C—$R^1$, preferably one is C—$R^1$, wherein $R^1$ is formula 2, then $X^3$ and $X^7$ are N, or $X^3$ and $X^5$ are N; or one of $X^1$, $X^2$, $X^3$, $X^3$, $X^4$, $X^5$, $X^6$, $X^7$ and $X^8$ are N, namely $X^3$ is N, $X^7$ is N, or $X^8$ is N, more preferred $X^3$ is N, or $X^7$ is N, and at least one is C—$R^1$ but not more than three are C—$R^1$, preferably one is C—$R^1$, wherein $R^1$ is formula 2.

According to one embodiment of formula 1, wherein at least one of $X^1$ to $X^8$ but not more than four, preferably not more than three or not more than two of $X^1$ to $X^8$ of the fluorene group are N and at least one to three are C—$R^1$, preferably one is C—$R^1$, with the provision:

if the fluorene group comprises one N atoms only and $X^1$ or $X^8$ is selected N, then $R^1$ is formula 2 and comprises at least one hetero atom selected from N, O or S, preferably N; and/or if the fluorene group comprises two N atoms only then $X^3$ and $X^7$, or $X^3$ and $X^5$ are selected N.

According to one embodiment of formula 1, wherein at least one of $X^1$ to $X^8$ but not more than four of $X^1$ to $X^8$ are N and at least one to three are C—$R^1$, preferably one is C—$R^1$, and wherein at least one of $R^1$ but not more than three of $R^1$, preferably one of $R^1$, are formula 2, with the provision regarding $X^1$ to $X^8$:

if one selected N, namely $X^1$ or $X^8$, then formula 2 comprises at least one hetero atom selected from N, O or S, preferably N; and/or if two selected N, then $X^3$ and $X^7$, or $X^3$ and $X^5$ are N.

According to one embodiment of formula 1, wherein at least one of $X^1$ to $X^8$ but not more than four of $X^1$ to $X^8$ are N and at least one to three are C—$R^1$, preferably one is C—$R^1$, and wherein at least one of $R^1$ but not more than three of $R^1$, preferably one of $R^1$, are formula 2, with the provision regarding $X^1$ to $X^8$:

if one selected N, namely $X^1$ or $X^8$, then formula 2 comprises at least one triazine group; and/or if two selected N, then $X^3$ and $X^7$, or $X^3$ and $X^5$ are N, then formula 2 comprises at least one triazine group.

According to one embodiment of formula 1, wherein one of $X^1$ to $X^8$ is N only and at least one to three are C—$R^1$, preferably one is C—$R^1$, and wherein at least one of $R^1$ but not more than three of $R^1$, preferably one of $R^1$, are formula 2, and wherein formula 2 comprises at least one triazine group.

According to one embodiment of formula 1, wherein one of $X^1$, $X^2$, $X^7$ or $X^8$ is N and one is C—$R^1$, wherein $R^1$ is formula 2, and wherein formula 2 comprises one triazine group.

According to one embodiment, the compound is represented by formula 1:

(1)

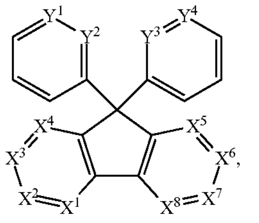

wherein $X^1$, $X^2$, $X^3$, $X^3$, $X^4$, $X^5$, $X^6$, $X^7$ and $X^8$ are independently selected from C—H, N, C—$R^1$, wherein $R^1$ are independently selected from CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, alkenyl, formula 2, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

wherein at least one of $X^1$ to $X^8$ but not more than four of $X^1$ to $X^8$ are N, and at least one is C—$R^1$ but not more than three are C—$R^1$, wherein $R^1$ is formula 2:

(2)

$$*—L{+}G]_n,$$

wherein L is a direct bond, phenylene, biphenylene, substituted or unsubstituted $C_6$ to $C_{18}$ arylene, substituted or unsubstituted $C_3$ to $C_{20}$ heteroarylene, or $C_6$ to $C_{40}$ alkenyl, wherein the substituents of the substituted $C_6$ to $C_{18}$ arylene and substituted $C_3$ to $C_{20}$ heteroarylene are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S;

wherein G is independently selected from unsubstituted or substituted $C_6$ to $C_{40}$ aryl or $C_3$ to $C_{42}$ heteroaryl, $C_6$ to $C_{40}$ alkenyl, CN, $PY(R^2)_2$ with Y being O or S wherein the substituents of the substituted $C_6$ to $C_{18}$ aryl and of the substituted $C_3$ to $C_{20}$ heteroaryl are independently selected from H, CN, F, deuterium, $C_6$ to $C_{18}$ aryl, $C_3$ to $C_{20}$ heteroaryl, $C_1$ to $C_{16}$ alkyl, $C_1$ to $C_{16}$ alkoxy, nitrile, and $PY(R^2)_2$ with Y being O or S;

n=0, 1, 2 or 3, preferably 1, 2 or 3, further preferred 1 or 2, in addition preferred 1 and more preferred 2;

$Y^1$, $Y^2Y^3$ and $Y^4$ are C—$R^3$, wherein $R^3$ is independently selected from H, CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, $C_6$ to $C_{40}$ alkenyl, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

or $Y^2$ and $Y^3$ are C and connected via a single bond or bridged by formula 3, (3)

wherein W is $CH_2$, C—$(CH_3)_2$, N—H, N—$R^4$, O or S, and $Y^1$ and $Y^4$ are C—H, wherein $R^4$ is selected from $C_1$ to $C_6$ alkyl, substituted or unsubstituted $C_6$ to $C_{18}$ aryl, substituted or unsubstituted $C_2$ to $C_{20}$ heteroaryl, wherein the substituents of the substituted $C_6$ to $C_{18}$ aryl and substituted $C_3$ to $C_{20}$ heteroaryl are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S;

and wherein the hetero atom is selected from N, O or S;

and wherein $R^2$ are the same or different and independently selected from the group consisting of $C_1$ to $C_{16}$ alkyl, $C_1$ to $C_{16}$ alkoxy, $C_6$ to $C_{26}$ alkenyl, $C_6$ to $C_{18}$ aryl and $C_3$ to $C_{25}$ heteroaryl.

If not otherwise stated H can represent hydrogen or deuterium.

If not otherwise stated the asterisk symbol "*" represents the binding position.

If not otherwise stated substituents of a substituted aryl, such as $C_6$ to $C_{18}$ aryl or there like; or substituents of a substituted heteroaryl, such as a $C_2$ to $C_{20}$ heteroaryl or $C_3$ to $C_{20}$ heteroaryl, or there like; can be independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen.

The compound can be an organic semiconductor or part of an organic semiconductor composition.

According to one embodiment, the compound is represented by formula 1:

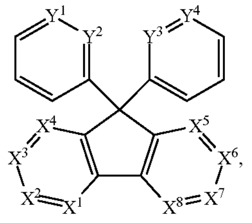

(1)

wherein $X^1$, $X^2$, $X^3$, $X^3$, $X^4$, $X^5$, $X^6$, $X^7$ and $X^8$ are independently selected from C—H, N, C—$R^1$, wherein $R^1$ are independently selected from CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, alkenyl, formula 2, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

wherein two of $X^1$, $X^2$, $X^3$, $X^3$, $X^4$, $X^5$, $X^6$, $X^7$ and $X^8$ are selected N, preferably $X^3$ and $X^7$ are N, or $X^3$ and $X^5$ are N; or one of $X^1$, $X^2$, $X^3$, $X^3$, $X^4$, $X^5$, $X^6$, $X^7$ and $X^8$ are N, preferably $X^3$ is N, or $X^7$ is N, or $X^8$ is N, and at least one is C—$R^1$ but not more than three are C—$R^1$, wherein $R^1$ is formula 2:

$$*\!-\!L\!+\!G]_n, \quad (2)$$

wherein L is a direct bond, phenylene, biphenylene, substituted or unsubstituted $C_6$ to $C_{18}$ arylene, substituted or unsubstituted $C_3$ to $C_{20}$ heteroarylene, or $C_6$ to $C_{40}$ alkenyl, wherein the substituents of the substituted $C_6$ to $C_{18}$ arylene and substituted $C_3$ to $C_{20}$ heteroarylene are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S;

wherein G is independently selected from unsubstituted or substituted $C_6$ to $C_{40}$ aryl or $C_3$ to $C_{42}$ heteroaryl, $C_6$ to $C_{40}$ alkenyl, CN, $PY(R^2)_2$ with Y being O or S wherein the substituents of the substituted $C_6$ to $C_{18}$ aryl and of the substituted $C_3$ to $C_{20}$ heteroaryl are independently selected from H, CN, F, deuterium, $C_6$ to $C_{18}$ aryl, $C_3$ to $C_{20}$ heteroaryl, $C_1$ to $C_{16}$ alkyl, $C_1$ to $C_{16}$ alkoxy, nitrile, and $PY(R^2)_2$ with Y being O or S;

n=0, 1, 2 or 3, preferably 1, 2 or 3, further preferred 1 or 2, in addition preferred 1 and more preferred 2;

$Y^1$, $Y^2Y^3$ and $Y^4$ are C—$R^3$, wherein $R^3$ is independently selected from H, CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, $C_6$ to $C_{40}$ alkenyl, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

or $Y^2$ and $Y^3$ are C and connected via a single bond or bridged by formula 3,

(3)

wherein W is $CH_2$, C—$(CH_3)_2$, N—H, N—$R^4$, O or S, and $Y^1$ and $Y^4$ are C—H, wherein $R^4$ is selected from $C_1$ to $C_6$ alkyl, substituted or unsubstituted $C_6$ to $C_{18}$ aryl, substituted or unsubstituted $C_2$ to $C_{20}$ heteroaryl, wherein the substituents of the substituted $C_6$ to $C_{18}$ aryl and substituted $C_3$ to $C_{20}$ heteroaryl are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S; or $Y^1$, $Y^2$ and $Y^3$ are C, wherein $Y^1$ and $Y^2$ are part of an annelated benzene ring and the annelated benzene ring is connected via a single bond to $Y^3$;

and wherein the hetero atom is selected from N, O or S;

and wherein $R^2$ are the same or different and independently selected from the group consisting of $C_1$ to $C_{16}$ alkyl, $C_1$ to $C_{16}$ alkoxy, $C_6$ to $C_{26}$ alkenyl, $C_6$ to $C_{18}$ aryl and $C_3$ to $C_{25}$ heteroaryl.

According to one embodiment, the compound is represented by formula 1, wherein two of $X^1$, $X^2$, $X^3$, $X^3$, $X^4$, $X^5$, $X^6$, $X^7$ and $X^8$ are selected N, preferably $X^3$ and $X^7$ are N, or $X^3$ and $X^5$ are N; or one of $X^1$, $X^2$, $X^3$, $X^3$, $X^4$, $X^5$, $X^6$, $X^7$ and $X^8$ are N, preferably $X^3$ is N, or $X^7$ is N, or $X^8$ is N.

According to one embodiment, the compound is represented by formula 1, wherein in formula 1:

one of $X^1$, $X^2$, $X^3$, $X^3$, $X^4$, $X^5$, $X^6$, $X^7$ and $X^8$ are selected N, then if $X^8$ is selected N or if $X^1$ is selected N, then formula 2 comprises at least one hetero atom selected from N, O or S; or two of $X^1$, $X^2$, $X^3$, $X^3$, $X^4$, $X^5$, $X^6$, $X^7$ and $X^8$ are selected N, then $X^3$ and $X^7$ are N, or $X^3$ and $X^5$ are N; or one of $X^1$, $X^2$, $X^3$, $X^3$, $X^4$, $X^5$, $X^6$, $X^7$ and $X^8$ are N, namely $X^3$ is N, $X^7$ is N, or $X^8$ is N, preferably $X^3$ is N, or $X^7$ is N.

According to one embodiment, the compound is represented by formula 1, wherein $X^3$ and $X^7$ are selected N only.

According to one embodiment, the compound is represented by formula 1, wherein $X^3$ and $X^5$ are selected N only.

According to one embodiment, the compound is represented by formula 1, wherein $X^3$ is selected N only.

According to one embodiment, the compound is represented by formula 1, wherein $X^5$ is selected N only.

According to one embodiment, the compound is represented by formula 1, wherein $X^7$ is selected N only.

According to one embodiment, the compound is represented by formula 1, wherein $X^8$ is selected N only.

According to one embodiment, the compound is represented by formula 1:

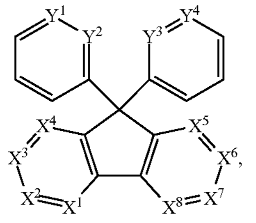

(1)

wherein $X^1$, $X^2$, $X^3$, $X^3$, $X^4$, $X^5$, $X^6$, $X^7$ and $X^8$ are independently selected from C—H, N, C—$R^1$, wherein $R^1$ are independently selected from CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, alkenyl, formula 2, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

wherein $X^3$ is N and at least one of $X^1$, $X^6$, $X^7$ or $X^8$ is $CR^1$ with $R^1$ being formula 2; or $X^7$ is N and at least one of $X^1$, $X^2$ or $X^3$ is $CR^1$ with $R^1$ being formula 2; or $X^8$ is N and at least one of $X^1$, $X^2$, $X^3$, $X^6$ is $CR^1$ with $R^1$ being formula 2; or one of $X^1$, $X^2$, $X^3$, $X^3$, $X^4$, $X^5$, $X^6$, $X^7$ or $X^8$ is $CR^1$ with $R^1$ being formula 2; or one of $X^3$, $X^6$ or $X^7$ is $CR^1$ with $R^1$ being formula 2, and wherein at least one of $R^1$ but not more than three of $R^1$ are formula 2:

$$*\!-\!L\!+\!G]_n, \qquad (2)$$

wherein L is a direct bond, phenylene, biphenylene, substituted or unsubstituted $C_6$ to $C_{18}$ arylene, substituted or unsubstituted $C_3$ to $C_{20}$ heteroarylene, or $C_6$ to $C_{40}$ alkenyl, wherein the substituents of the substituted $C_6$ to $C_{18}$ arylene and substituted $C_3$ to $C_{20}$ heteroarylene are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S;

wherein G is independently selected from unsubstituted or substituted $C_6$ to $C_{40}$ aryl or $C_3$ to $C_{42}$ heteroaryl, $C_6$ to $C_{40}$ alkenyl, CN, $PY(R^2)_2$ with Y being O or S wherein the substituents of the substituted $C_6$ to $C_{18}$ aryl and of the substituted $C_3$ to $C_{20}$ heteroaryl are independently selected from H, CN, F, deuterium, $C_6$ to $C_{18}$ aryl, $C_3$ to $C_{20}$ heteroaryl, $C_1$ to $C_{16}$ alkyl, $C_1$ to $C_{16}$ alkoxy, nitrile, and $PY(R^2)_2$ with Y being O or S;

n=0, 1, 2 or 3, preferably 1, 2 or 3, further preferred 1 or 2, in addition preferred 1 and more preferred 2;

$Y^1$, $Y^2Y^3$ and $Y^4$ are C—$R^3$, wherein $R^3$ is independently selected from H, CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, $C_6$ to $C_{40}$ alkenyl, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

or $Y^2$ and $Y^3$ are C and connected via a single bond or bridged by formula 3,

(3)

wherein W is $CH_2$, C—$(CH_3)_2$, N—H, N—$R^4$, O or S, and $Y^1$ and $Y^4$ are C—H, wherein $R^4$ is selected from $C_1$ to $C_6$ alkyl, substituted or unsubstituted $C_6$ to $C_{18}$ aryl, substituted or unsubstituted $C_2$ to $C_{20}$ heteroaryl, wherein the substituents of the substituted $C_6$ to $C_{18}$ aryl and substituted $C_3$ to $C_{20}$ heteroaryl are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S; or $Y^1$, $Y^2$ and $Y^3$ are C, wherein $Y^1$ and $Y^2$ are part of an annelated benzene ring and the annelated benzene ring is connected via a single bond to $Y^3$;

and wherein the hetero atom is selected from N, O or S;

and wherein $R^2$ are the same or different and independently selected from the group consisting of $C_1$ to $C_{16}$ alkyl, $C_1$ to $C_{16}$ alkoxy, $C_6$ to $C_{26}$ alkenyl, $C_6$ to $C_{18}$ aryl and $C_3$ to $C_{25}$ heteroaryl.

According to one embodiment, the compound is represented by formula 1, wherein at least one of $X^1$ to $X^8$ but not more than four of $X^1$ to $X^8$ are N, and at least one is C—$R^1$ but not more than three are C—$R^1$, wherein $R^1$ is formula 2; or $X^3$ is N and at least one of $X^1$, $X^6$, $X^7$ or $X^8$ is $CR^1$ with $R^1$ being formula 2; or $X^7$ is N and at least one of $X^1$, $X^2$ or $X^3$ is $CR^1$ with $R^1$ being formula 2; or $X^8$ is N and at least one of $X^1$, $X^2$, $X^3$, $X^6$ is $CR^1$ with $R^1$ being formula 2; or one of $X^1$, $X^2$, $X^3$, $X^3$, $X^4$, $X^5$, $X^6$, $X^7$ or $X^8$ is $CR^1$ with $R^1$ being formula 2; or one of $X^3$, $X^6$ or $X^7$ is $CR^1$ with $R^1$ being formula 2.

According to one embodiment, the compound is represented by formula 1, wherein $X^3$ is selected N only and at least one of $X^1$, $X^6$, $X^7$ or $X^8$ is $CR^1$ with $R^1$ being formula 2.

According to one embodiment, the compound is represented by formula 1, wherein $X^7$ is selected N only and at least one of $X^1$, $X^6$, $X^7$ or $X^8$ is $CR^1$ with $R^1$ being formula 2.

According to one embodiment, the compound is represented by formula 1, wherein $X^8$ is selected N only and at least one of $X^1$, $X^6$, $X^7$ or $X^8$ is $CR^1$ with $R^1$ being formula 2.

According to one embodiment, the compound is represented by formula 1, wherein one of $X^1$, $X^2$, $X^3$, $X^3$, $X^4$, $X^5$, $X^6$, $X^7$ or $X^8$ is $CR^1$ with $R^1$ being formula 2.

According to one embodiment, the compound is represented by formula 1, wherein one of $X^3$, $X^6$ or $X^7$ is $CR^1$ with $R^1$ being formula 2.

According to one embodiment, the compound is represented by formula 1:

(1)

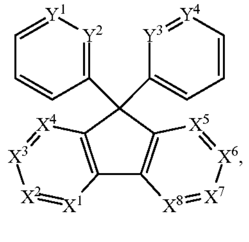

wherein $X^1$, $X^2$, $X^3$, $X^3$, $X^4$, $X^5$, $X^6$, $X^7$ and $X^8$ are independently selected from C—H, N, C—$R^1$, wherein $R^1$ are independently selected from CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, alkenyl, formula 2, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

wherein at least one of $X^1$ to $X^8$ but not more than four of $X^1$ to $X^8$ are N, and at least one is C—$R^1$ but not more than three are C—$R^1$, wherein $R^1$ is formula 2:

$$*-L-[G]_n, \quad (2)$$

wherein L is a direct bond, phenylene, biphenylene, substituted or unsubstituted $C_6$ to $C_{12}$ arylene, preferably $C_6$ arylene, or substituted or unsubstituted $C_3$ to $C_{11}$ heteroarylene, preferably $C_3$ to $C_5$ heteroarylene, wherein the hetero atom of the heteroarylene is N, and wherein the substituents of the substituted arylene and of the substituted heteroaryl are independently selected from, $C_6$ to $C_{12}$ aryl, $C_3$ to $C_{11}$ heteroaryl, $C_1$ to $C_5$ alkyl, $C_1$ to $C_5$ alkoxy, nitrile, and $PY(R^2)_2$ with Y being O or S;

wherein G is independently selected from unsubstituted or substituted $C_6$ to $C_{40}$ aryl or $C_3$ to $C_{42}$ heteroaryl, $C_6$ to $C_{40}$ alkenyl, CN, $PY(R^2)_2$ with Y being O or S wherein the substituents of the substituted $C_6$ to $C_{18}$ aryl and of the substituted $C_3$ to $C_{20}$ heteroaryl are independently selected from H, CN, F, deuterium, $C_6$ to $C_{18}$ aryl, $C_3$ to $C_{20}$ heteroaryl, $C_1$ to $C_{16}$ alkyl, $C_1$ to $C_{16}$ alkoxy, nitrile, and $PY(R^2)_2$ with Y being O or S;

n=0, 1, 2 or 3, preferably 1, 2 or 3, further preferred 1 or 2, in addition preferred 1 and more preferred 2;

$Y^1$, $Y^2Y^3$ and $Y^4$ are C—$R^3$, wherein $R^3$ is independently selected from H, CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, $C_6$ to $C_{40}$ alkenyl, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

or $Y^2$ and $Y^3$ are C and connected via a single bond or bridged by formula 3, (3)

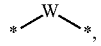

wherein W is $CH_2$, C—$(CH_3)_2$, N—H, N—$R^4$, O or S, and $Y^1$ and $Y^4$ are C—H, wherein $R^4$ is selected from $C_1$ to $C_6$ alkyl, substituted or unsubstituted $C_6$ to $C_{18}$ aryl, substituted or unsubstituted $C_2$ to $C_{20}$ heteroaryl, wherein the substituents of the substituted $C_6$ to $C_{18}$ aryl and substituted $C_3$ to $C_{20}$ heteroaryl are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S; or $Y^1$, $Y^2$ and $Y^3$ are C, wherein $Y^1$ and $Y^2$ are part of an annelated benzene ring and the annelated benzene ring is connected via a single bond to $Y^3$;

and wherein the hetero atom is selected from N, O or S;

and wherein $R^2$ are the same or different and independently selected from the group consisting of $C_1$ to $C_3$ alkyl, $C_1$ to $C_3$ alkoxy, $C_6$ to $C_{12}$ aryl and $C_3$ to $C_{11}$ heteroaryl.

According to one embodiment, the compound is represented by formula 1, wherein L is a direct bond, phenylene, biphenylene, substituted or unsubstituted $C_6$ to $C_{12}$ arylene, preferably $C_6$ arylene, or substituted or unsubstituted $C_3$ to $C_{11}$ heteroarylene, preferably $C_3$ to $C_5$ heteroarylene, wherein the hetero atom of the heteroarylene is N, and wherein the substituents of the substituted arylene and of the substituted heteroaryl are independently selected from, $C_6$ to $C_{12}$ aryl, $C_3$ to $C_{11}$ heteroaryl, $C_1$ to $C_5$ alkyl, $C_1$ to $C_5$ alkoxy, nitrile, and $PY(R^2)_2$ with Y being O or S, and wherein the $R^2$ are independently selected from the group consisting of $C_1$ to $C_3$ alkyl, $C_1$ to $C_3$ alkoxy, $C_6$ to Cu aryl and $C_3$ to $C_{11}$ heteroaryl.

According to one embodiment, the compound is represented by formula 1, wherein L is a direct bond. According to one embodiment, the compound is represented by formula 1, wherein L is a direct bond. According to one embodiment, the compound is represented by formula 1, wherein L is a phenylene or biphenylene. According to one embodiment, the compound is represented by formula 1, wherein L is a substituted or unsubstituted $C_6$ to Cu arylene. According to one embodiment, the compound is represented by formula 1, wherein L is a substituted or unsubstituted $C_6$ arylene. According to one embodiment, the compound is represented by formula 1, wherein L is a substituted or unsubstituted substituted or unsubstituted $C_3$ to $C_{11}$ heteroarylene. According to one embodiment, the compound is represented by formula 1, wherein L is a substituted or unsubstituted substituted or unsubstituted $C_3$ to $C_5$ heteroarylene. According to one embodiment, the compound is represented by formula 1, wherein L is a substituted or unsubstituted substituted or unsubstituted $C_3$ to $C_{11}$ heteroarylene, wherein the hetero atom of the heteroarylene is N. According to one embodiment, the compound is represented by formula 1, wherein L is a substituted or unsubstituted substituted or unsubstituted $C_3$ to $C_5$ heteroarylene, wherein the hetero atom of the heteroarylene is N. The substituents of the substituted arylene and of the substituted heteroaryl are independently selected from, $C_6$ to $C_{12}$ aryl, $C_3$ to $C_{11}$ heteroaryl, $C_1$ to $C_5$ alkyl, $C_1$ to $C_5$ alkoxy, nitrile, and $PY(R^2)_2$ with Y being O or S, wherein the $R^2$ are independently selected from the group consisting of $C_1$ to $C_3$ alkyl, $C_1$ to $C_3$ alkoxy, $C_6$ to Cu aryl and $C_3$ to $C_{11}$ heteroaryl.

According to one embodiment, the compound is represented by formula 1, wherein L is independently selected from the group comprising F1 to F12:

(F1)

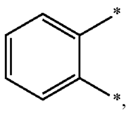

(F2)

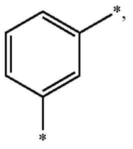

(F3)

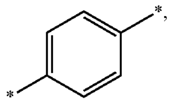

(F4)

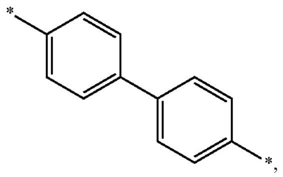

(F5)

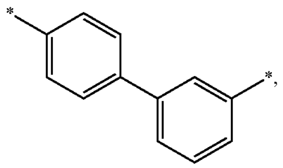

(F6)

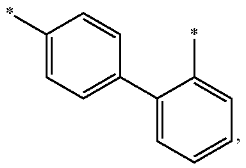

(F7)

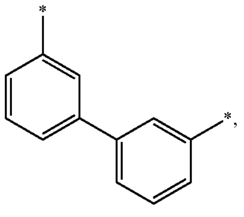

(F8)

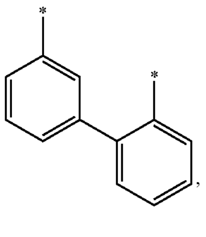

-continued (F9)

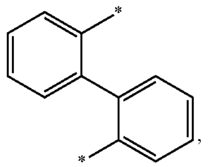

(F10)

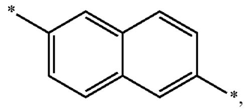

(F11)

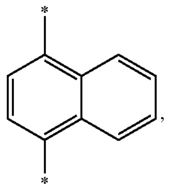

(F12)

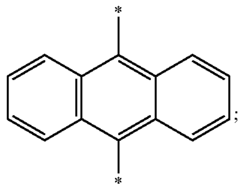

preferably L is selected from F2, F3, F4, F5 or F7, more preferably L is selected from F2, F3, F5 or F7, more preferred L is selected from F2 or F3.

According to one embodiment, the compound is represented by formula 1, wherein L is selected from F2, F3, F5 or F7. According to one embodiment, the compound is represented by formula 1, wherein L is selected from F2 or F3.

According to one embodiment, the compound is represented by formula 1.

(1)

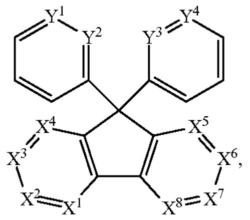

wherein $X^1$, $X^2$, $X^3$, $X^3$, $X^4$, $X^5$, $X^6$, $X^7$ and $X^8$ are independently selected from C—H, N, C—$R^1$, wherein pare independently selected from CN, F, deuterium, substituted or unsubstituted $C_1$ to $C_{18}$ aryl, substituted or unsubstituted $C_3$ to $C_2$ heteroaryl, $C_1$-$C_{16}$ alkyl, $C_1$ to $C_{16}$ alkoxy, alkenyl, formula 2, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

wherein at least one of $X^1$ to $X^8$ but not more than four of $X^1$ to $X^8$ are N, and at least one is C—$R^1$ but not more than three are C—$R^1$, wherein $R^1$ is formula 2:

$$*—L-[G]_n, \quad (2)$$

wherein L is a direct bond, phenylene or biphenylene, substituted or unsubstituted $C_6$ to $C_{18}$ arylene, substituted or unsubstituted $C_3$ to $C_{20}$ heteroarylene, or $C_6$ to $C_{40}$ alkenyl, wherein the substituents of the substituted $C_6$ to $C_{18}$ arylene and substituted $C_3$ to $C_{20}$ heteroarylene are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S;

wherein G is independently selected from unsubstituted or substituted triazine, pyrazine, acridine, benzoacridine, dibenzoacridine, phenanthroline, benzimidazole and carbazole, wherein the substituents are independently selected from H, CN, F, deuterium, $C_6$ to $C_{18}$ aryl, $C_3$ to $C_{20}$ heteroaryl, $C_1$ to $C_{16}$ alkyl, $C_1$ to $C_{16}$ alkoxy, nitrile, and $PY(R^2)_2$ with Y being O or S;

n=0, 1, 2 or 3, preferably 1, 2 or 3, further preferred 1 or 2, in addition preferred 1 and more preferred 2;

$Y^1$, $Y^2Y^3$ and $Y^4$ are C—$R^3$, wherein $R^3$ is independently selected from H, CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, $C_6$ to $C_{40}$ alkenyl, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

or $Y^2$ and $Y^3$ are C and connected via a single bond or bridged by formula 3,

(3)

wherein W is $CH_2$, C—$(CH_3)_2$, N—H, N—$R^4$, O or S, and $Y^1$ and $Y^4$ are C—H, wherein $R^4$ is selected from $C_1$ to $C_6$ alkyl, substituted or unsubstituted $C_6$ to $C_{18}$ aryl, substituted or unsubstituted $C_2$ to $C_{20}$ heteroaryl, wherein the substituents of the substituted $C_6$ to $C_{18}$ aryl and substituted $C_3$ to $C_{20}$ heteroaryl are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S; or $Y^1$, $Y^2$ and $Y^3$ are C, wherein $Y^1$ and $Y^2$ are part of an annelated benzene ring and the annelated benzene ring is connected via a single bond to $Y^3$;

and wherein the hetero atom is selected from N, O or S;

and wherein $R^2$ are the same or different and independently selected from the group consisting of $C_1$ to $C_{16}$ alkyl, $C_1$ to $C_{16}$ alkoxy, $C_6$ to $C_{26}$ alkenyl, $C_6$ to $C_{18}$ aryl and $C_3$ to $C_{25}$ heteroaryl.

According to one embodiment, the compound is represented by formula 1:

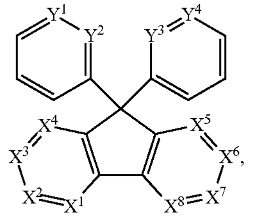

(1)

wherein $X^1$, $X^2$, $X^3$, $X^3$, $X^4$, $X^5$, $X^6$, $X^7$ and $X^8$ are independently selected from C—H, N, C—$R^1$, wherein $R^1$ are independently selected from CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, alkenyl, formula 2, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

wherein at least one of $X^1$ to $X^8$ but not more than four of $X^1$ to $X^8$ are N, and at least one is C—$R^1$ but not more than three are C—$R^1$, wherein $R^1$ is formula 2:

$$*—L-[G]_n, \quad (2)$$

wherein L is a direct bond, phenylene or biphenylene, preferably phenylene or biphenylene;

wherein G is independently selected from triazine, pyrazine, acridine, benzoacridine, dibenzoacridine, phenanthroline, benzimidazole and carbazole;

n=1, 2 or 3, preferably 1 or 2, in addition preferred 1 and more preferred 2;

$Y^1$, $Y^2Y^3$ and $Y^4$ are C—$R^3$, wherein $R^3$ is independently selected from H, CN, F, deuterium, substituted or unsubstituted $C_6$ to $C_{18}$ aryl, substituted or unsubstituted $C_3$ to $C_{20}$ heteroaryl, $C_1$-$C_{16}$ alkyl, $C_1$ to $C_{16}$ alkoxy, $C_6$ to $C_{40}$ alkenyl, nitrile, amino, $PY(R^2)_2$ with Y being O or S, wherein the substituents of the substituted $C_6$ to $C_{18}$ aryl and of the substituted $C_3$ to $C_{20}$ heteroaryl are independently selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{18}$ aryl, perhalogenated $C_6$ to $C_{18}$ aryl, $C_3$ to $C_{24}$ heteroaryl, CN, halogen;

or $Y^2$ and $Y^3$ are C and connected via a single bond or bridged by formula 3,

(3)

wherein W is $CH_2$, C—$(CH_3)_2$, N—H, N—$R^4$, O or S, and $Y^1$ and $Y^4$ are C—H, wherein $R^4$ is selected from $C_1$ to $C_6$ alkyl, substituted or unsubstituted $C_6$ to $C_{18}$ aryl, substituted or unsubstituted $C_2$ to $C_{20}$ heteroaryl, wherein the substituents of the substituted $C_6$ to $C_{18}$ aryl and substituted $C_3$ to $C_{20}$ heteroaryl are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —PY($R^2$)$_2$ with Y being O or S; or $Y^1$, $Y^2$ and $Y^3$ are C, wherein $Y^1$ and $Y^2$ are part of an annelated benzene ring and the annelated benzene ring is connected via a single bond to $Y^3$;

and wherein the hetero atom is selected from N, O or S;

and wherein $R^2$ are the same or different and independently selected from the group consisting of $C_1$ to $C_{16}$ alkyl, $C_1$ to $C_{16}$ alkoxy, $C_6$ to $C_{26}$ alkenyl, $C_6$ to $C_{18}$ aryl and $C_3$ to $C_{25}$ heteroaryl.

According to one embodiment, the compound is represented by formula 1, wherein $Y^1$, $Y^2$ and $Y^3$ are C, and wherein $Y^1$ and $Y^2$ are part of an annelated benzene ring and the annelated benzene ring is connected via a single bond to $Y^3$ is excluded.

According to one embodiment, the compound represented by formula 1 may be free of a $SO_2$ group.

According to one embodiment, the compound represented by formula 1, wherein $X^1$ and $X^2$ may be not N.

According to one embodiment, the compound is represented by formula 1, wherein G is selected from the group comprising triazine, pyrazine, acridine, benzoacridine, dibenzoacridine, phenanthroline, benzimidazole and carbazole.

According to one embodiment, the compound is represented by formula 1, wherein G is selected from the group comprising D1 to D43, wherein G is bonded at anyone of the C atoms of D1 to D43 via a single bond to L:

(D1)

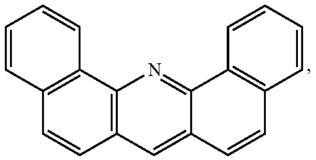

(D2)

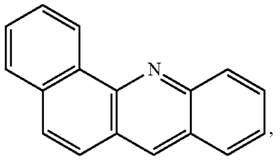

(D3)

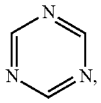

(D4)

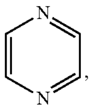

(D5)

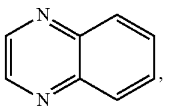

-continued (D6)

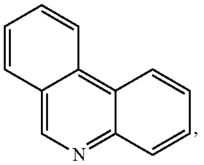

(D7)

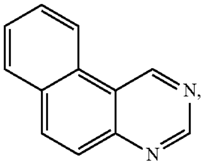

(D8)

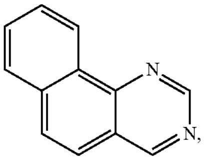

(D9)

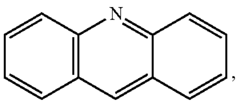

(D10)

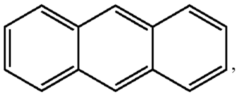

(D11)

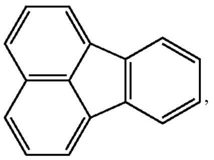

(D12)

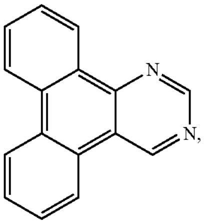

(D13)

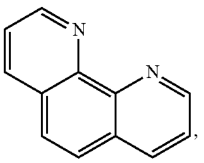

(D14)

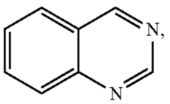

(D15)

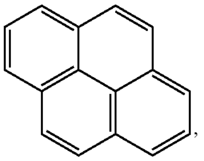

-continued
(D16)
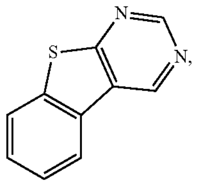
(D17)
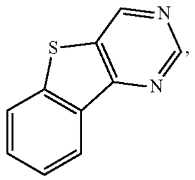
(D18)
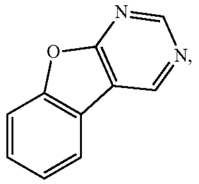
(D19)
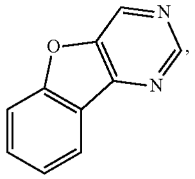
(D20)
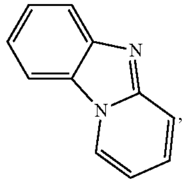
(D21)
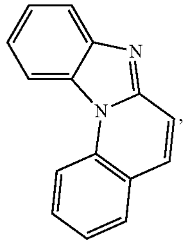
-continued
(D22)
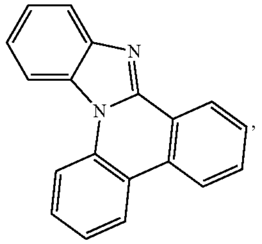
(D23)
CN,
(D24)
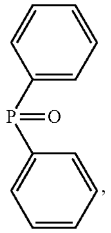
(D25)
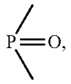
(D26)
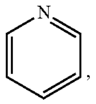
(D27)
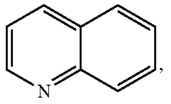
(D28)
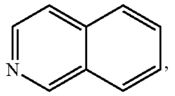
(D29)
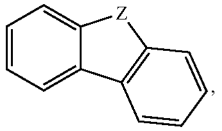
(D30)
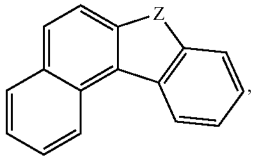
(D31)
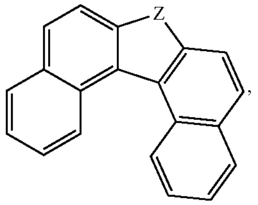

-continued (D32)

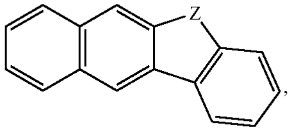

(D33)

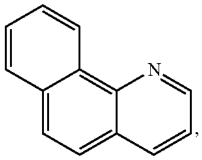

(D34)

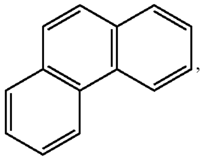

(D35)

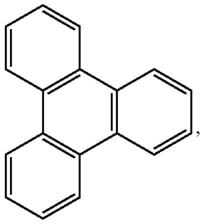

(D36)

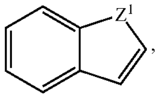

(D37)

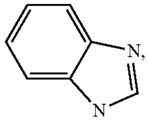

(D38)

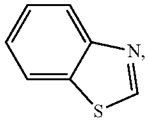

(D39)

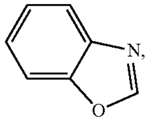

(D40)

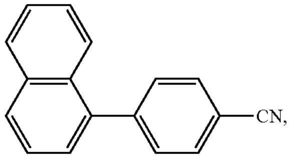

(D41)

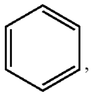

-continued (D42)

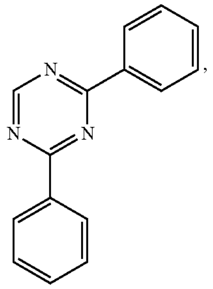

(D43)

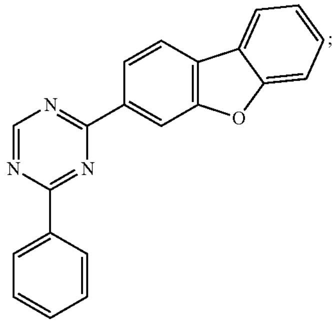

and wherein Z is selected from O, S, Se, $SiR_2$, $CR_2$, and $NR_2$; and wherein $Z^1$ is selected from O, S, and NR; wherein R is selected from $C_1$ to $C_6$ alkyl, $C_6$ to $C_{18}$ aryl, $C_2$ to $C_{20}$ heteroaryl.

According to one embodiment, the compound is represented by formula 1, wherein L is selected from F2, F3, F5 or F7, preferably L is selected from F2 or F3; and G is selected from the group comprising D1 to D43, preferably G is selected from the group comprising D1 to D25 and more preferred D1 to D5.

According to one embodiment, the compound is represented by formula 1, wherein n=0, 1 or 2, preferably n=0 or 1 and further preferred n=1.

According to another embodiment, the compound is represented by formula 1, wherein n=0, 1 or 2, preferably 1, 2 or 3, further preferred 1 or 2, in addition preferred 1 and more preferred 2.

According to another embodiment, wherein the compounds of formula 1 are represented by formula 5 to 8, wherein W is selected from C—$(CH_3)_2$, N—$R^4$, O or S, and $Y^1$ to $Y^4$ are C—$R^3$ (5)

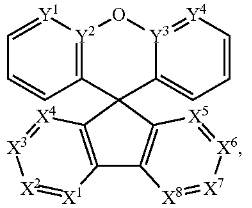

(6)

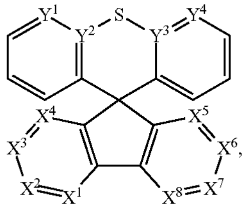

-continued (7)

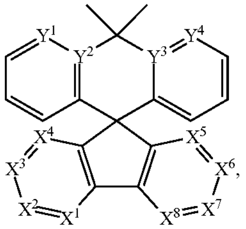

(8)

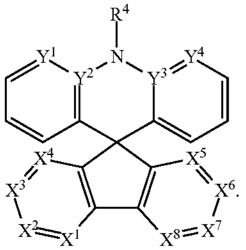

According to another embodiment of the compound of formula 1, wherein the hetero atom of the $C_3$ to $C_{24}$ heteroaryl, $C_3$ to $C_{12}$ heteroaryl, $C_3$ to $C_{12}$ heteroarylene, may be selected from N, O or S.

According to another embodiment of the compound of formula 1, wherein the hetero atom of the $C_3$ to $C_{24}$ heteroaryl, $C_3$ to $C_{12}$ heteroaryl, $C_3$ to $C_{12}$ heteroarylene, may be selected from N or O.

According to another embodiment of the compound of formula 1, wherein $R^2$, $R^3$, $R^4$, may be independently selected from substituted or unsubstituted $C_1$ to $C_{16}$ alkyl, substituted or unsubstituted $C_6$ to $C_{12}$ aryl, substituted or unsubstituted $C_3$ to $C_{17}$ heteroaryl, wherein the substituents of the substituted $C_6$ to $C_{12}$ aryl and substituted $C_3$ to $C_{17}$ heteroarylene are selected from $C_1$ to $C_{12}$ alkyl, perhalogenated $C_1$ to $C_{12}$ alkyl, $C_1$ to $C_{12}$ alkoxy, perhalogenated $C_1$ to $C_{12}$ alkoxy, $C_6$ to $C_{24}$ aryl, perhalogenated $C_6$ to $C_{24}$ aryl, $C_3$ to $C_{24}$ heteroaryl, CN, halogen, P(=O)R'R", C(=O)R' or C(=O)OR', wherein R' and R" are independently selected from $C_1$ to $C_{16}$ alkyl, $C_6$ to $C_{24}$ aryl, $C_3$ to $C_{24}$ heteroaryl.

According to another embodiment of the compound of formula 1, wherein $R^2$, $R^3$, $R^4$ may be independently selected from H, D, unsubstituted $C_6$ to $C_{18}$ aryl, or unsubstituted $C_3$ to $C_{24}$ heteroaryl. According to another embodiment of the compound of formula 1, wherein $R^1$, $R^2$ may be preferably independently selected from H, D, or unsubstituted $C_6$ to $C_{18}$ aryl.

According to another embodiment of the compound of formula 1, wherein $R^1$, $R^2$ may be further preferred independently selected from H, D, or unsubstituted $C_6$ aryl.

According to another embodiment of the compound of formula 1, wherein $R^2$, $R^3$, $R^4$ may in addition preferred independently selected from H or D and $R^2$ is a unsubstituted $C_6$ aryl.

According to another embodiment of the compound of formula 1, wherein $R^2$, $R^3$, $R^4$ may in addition selected from H or D.

According to one embodiment, the compound is represented by formula 1, wherein the number of aromatic 6 member rings is 5 to 15, preferably 6 to 12, further preferred 7 to 11 and also preferred 8 to 10 or 6 to 9.

According to one embodiment, the compound is represented by formula 1, wherein the number of non-hetero aromatic 6 member rings is 6 to 15, preferably 7 to 12, further preferred 7 to 11 and also preferred 8 to 10 or 6 to 9.

According to one embodiment, the compound is represented by formula 1, wherein the number of hetero aromatic 6 member rings is 1 to 4, preferably 1 to 3, further preferred 1, 2 or 3, in addition preferred 2 and also preferred 3.

According to one embodiment, the compound is represented by formula 1, wherein the number of non-hetero aromatic 6 member rings is 6 to 15, preferably 7 to 12, further preferred 7 to 11 and also preferred 8 to 10 or 6 to 9 and the number of hetero aromatic 6 member rings is 1 to 4, preferably 1 to 3, further preferred 1, 2 or 3, in addition preferred 2 and also preferred 3.

According to another embodiment the compound of formula 1 may be selected from G1 to G8:

(G1)

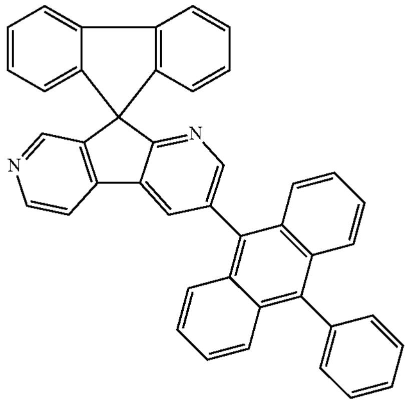

, (G2)

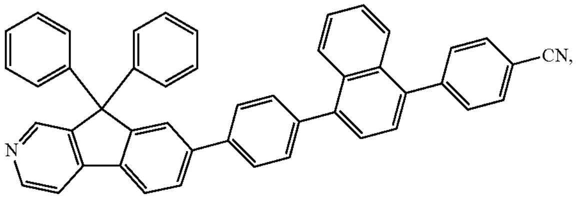

(G3)

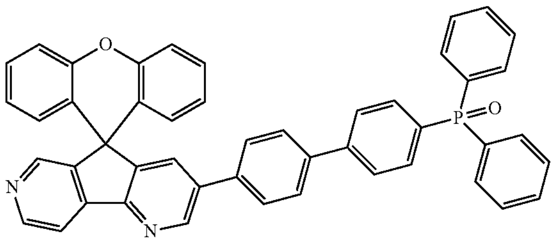

, (G4)

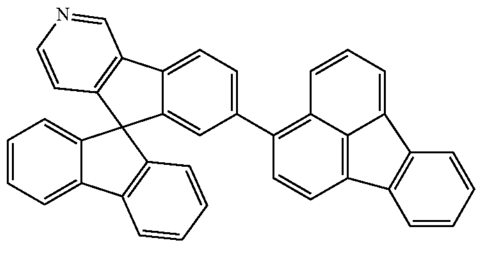

,

-continued (G5)

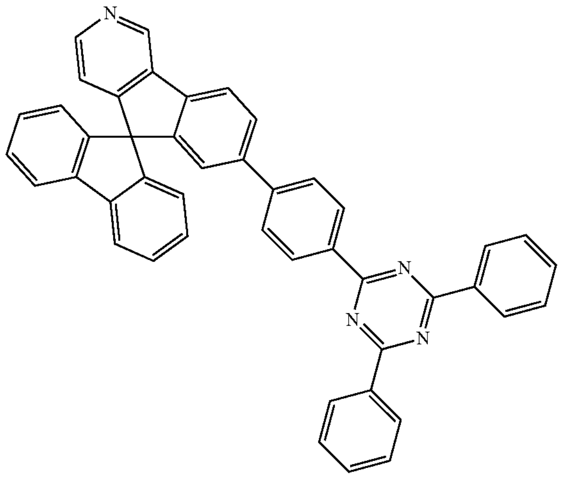

, (G6)

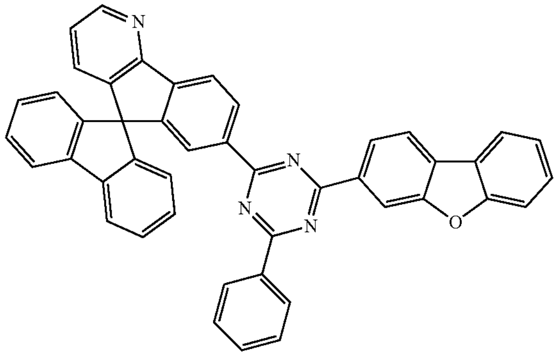

, (G7)

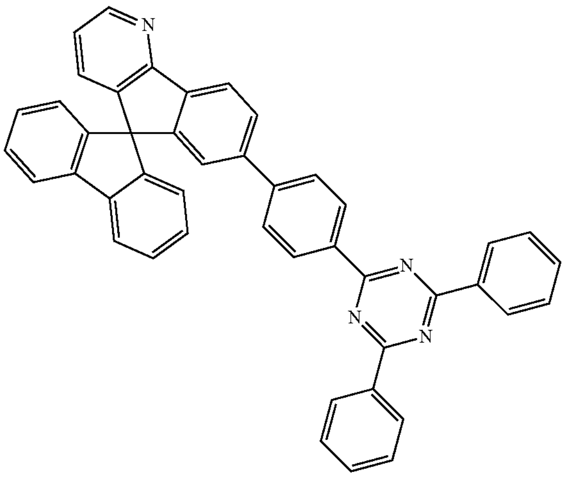

,

-continued (G8)

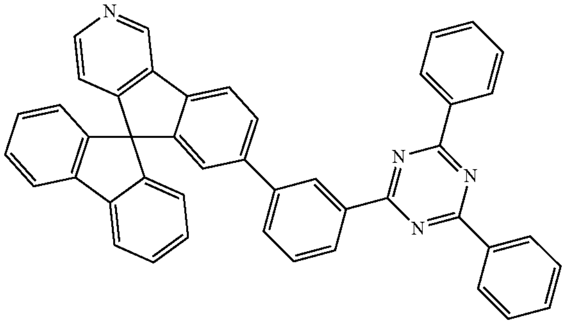

.

According to another aspect, an organic semiconductor layer comprises at least one compound of formula 1.

According to an embodiment the organic semiconductor layer comprises at least one compound of formula 1, wherein the organic semiconductor layer can be a charge transport layer.

According to an embodiment the organic semiconductor layer comprises at least one compound of formula 1, wherein the organic semiconductor layer can be a charge transport layer, wherein the charge transport layer can be preferably an electron transport layer (ETL).

According to an embodiment the organic semiconductor layer comprises at least one compound of formula 1, wherein the organic semiconductor layer can be a charge transport layer, wherein the charge transport layer can be an electron injection layer (EIL).

According to an embodiment the organic semiconductor layer may comprise a dopant or an additive.

According to another embodiment the organic semiconductor layer does not contain a dopant and/or an additive.

According to another embodiment the organic semiconductor layer may comprise a first component that is a compound of formula 1 and addition at least one second component that differs from the compound of formula 1.

According to another embodiment the organic semiconductor layer may comprise a first component that is a compound of formula 1 and addition at least one second component that differs from the compound of formula 1, wherein the at least one second component may be selected from the group comprising a metal, metal salt, a metal complex, or a matrix material that differs from the compound of formula 1.

According to an embodiment the organic semiconductor layer comprises a) at least one compound of formula 1, and in addition b) at least one organic metal complex.

According to an embodiment the organic semiconductor layer comprises a) at least one compound of formula 1, and in addition b) at least one organic metal complex, wherein the metal of the organic metal complex is selected from alkali or alkaline earth metal, more preferably the metal is lithium, magnesium or calcium.

According to one embodiment the organic semiconductor layer comprises a compound of formula 1 and an organic metal complex, wherein the metal of the organic metal complex is selected from alkali, alkaline earth or rare earth metal, more preferably the metal is an alkali or alkaline earth metal.

According to an embodiment the organic semiconductor layer comprises a) at least one compound of formula 1, and in addition b) at least one organic metal complex, wherein the organic metal complex comprises at least one ligand, wherein the ligand is selected from a quinolate or borate group.

Quinolates that can be suitable used are disclosed in WO 2013079217 A1 and incorporated by reference.

Borate groups that can be suitable used are disclosed in WO 2013079676 A1.

According to an embodiment the organic semiconductor layer comprises a) at least one compound of formula 1, and in addition b) at least one organic metal complex, wherein the organic metal complex the following formula 9:

Formula (9)

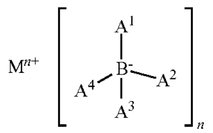

wherein M is a metal ion, each of $A^1$-$A^4$ is independently selected from H, substituted or unsubstituted $C_6$ to $C_{20}$ aryl and substituted or unsubstituted $C_2$ to $C_{20}$ heteroaryl and n is valence of the metal ion.

According to one embodiment of formula (9), wherein n is 1 or 2.

According to one embodiment of formula (9), wherein M is an alkali metal, an alkaline earth metal or a rare earth metal, alternatively an alkali metal or alkaline earth metal, alternatively selected from lithium, magnesium or calcium.

According to one embodiment of formula (9), wherein at least three groups selected from $A^1$ to $A^4$ are nitrogen containing heteroaryl.

According to one embodiment, wherein the heteroaryl of Formula (9) contains a nitrogen and the nitrogen containing heteroaryl is bound to the central boron atom via a N—N bond, preferably the heteroaryl in Formula (9) is pyrazolyl.

The compound of formula (1) and/or the organic metal complex may be essentially non-emissive.

According to another aspect an organic semiconductor layer may comprise at least one or two compounds according to formula 1 of the present invention.

The organic semiconductor layer comprising the at least one compound of formula 1, or a composition comprising a) at least one compound of formula 1 and in addition b) at least one organic metal complex, may be essentially non-emissive.

The thickness of the organic semiconductor layer may be from about 0.5 nm to about 100 nm, for example about 2 nm to about 40 nm. When the thickness of the organic semiconductor layer is within these ranges, the organic semiconductor layer may have improved charge transport ability without a substantial increase in operating voltage.

The organic semiconductor layer comprising the at least one compound of formula 1, or the composition comprising a) at least one compound of formula 1 and in addition b) at least one organic metal complex, may have strong electron transport characteristics to increase charge mobility and/or stability.

According to another aspect an electronic device may comprise at least one organic semiconductor layer of the present invention.

According to another aspect an electronic device may comprise at least one anode and at least one cathode, preferably the organic semiconductor layer is arranged between the anode and the cathode.

The organic semiconductor layer comprising a compound of the present invention may have strong electron transport characteristics to increase charge mobility and/or stability and thereby to improve luminance efficiency, voltage characteristics, and/or lifetime characteristics of an electronic device.

The electronic device of the present invention may further comprise a photoactive layer, wherein the organic semiconductor layer of the present invention is arranged between the photoactive layer and the cathode layer, preferably between an emission layer or light-absorbing layer and the cathode layer, preferably the organic semiconductor layer is an electron transport layer.

An organic electronic device according to one embodiment comprises the organic semiconductor layer of the present invention, at least one anode layer, at least one cathode layer and at least one emission layer, wherein the organic semiconductor layer is preferably arranged between the emission layer and the cathode layer.

An organic electronic device according to one embodiment can be a light emitting device, thin film transistor, a battery, a display device or a photovoltaic cell, and preferably a light emitting device. A light emitting device can be an OLED.

According to one embodiment the OLED may have the following layer structure, wherein the layers having the following order:

an anode layer, a hole injection layer, optional a first hole transport layer, optional a second hole transport layer, an emission layer, an electron transport layer comprising the compound according to the invention, an electron injection layer, and a cathode layer.

According to another aspect of the present invention, there is provided a method of manufacturing an organic electronic device, the method using:

at least one deposition source, preferably two deposition sources and more preferred at least three deposition sources.

The methods for deposition that can be suitable comprise:

deposition via vacuum thermal evaporation;

deposition via solution processing, preferably the processing is selected from spin-coating, printing, casting; and/or slot-die coating.

According to various embodiments of the present invention, there is provided a method using:

a first deposition source to release the compound of formula 1 according to the invention, and a second deposition source to release the at least one organic metal complex; the method comprising the steps of forming the electron transport layer stack; whereby for an organic light-emitting diode (OLED):

the first electron transport layer is formed by releasing the compound of formula 1 from the first deposition source and the organic metal complex from the second deposition source.

According to various embodiments of the present invention, the method may further include forming on the anode electrode an emission layer and at least one layer selected from the group consisting of forming a hole injection layer, forming a hole transport layer, or forming a hole blocking layer, between the anode electrode and the organic semiconductor layer.

According to various embodiments of the present invention, the method may further include the steps for forming an organic light-emitting diode (OLED), wherein on a substrate a first anode electrode is formed, on the first anode electrode an emission layer is formed, on the emission layer an electron transport layer stack is formed, preferably a first electron transport layer is formed on the emission layer and a second electron transport layer is formed on the first electron transport layer and the second electron transport layer comprises the compound according to the invention, and finally a cathode electrode is formed, optional a hole injection layer, a hole transport layer, and a hole blocking layer, formed in that order between the first anode electrode and the emission layer, optional an electron injection layer is formed between the electron transport layer stack and the cathode electrode.

According to various embodiments of the present invention, the method may further include forming an electron injection layer on a first electron transport layer. However, according to various embodiments of the OLED of the present invention, the OLED may not comprise an electron injection layer.

According to another embodiment, it is provided an organic electronic device comprising at least one organic semiconductor layer comprising a compound according to formula 1.

According to another embodiment, it is provided an organic electronic device comprising at least one organic semiconductor layer comprising a compound according to formula 1, wherein the organic semiconductor layer may be comprised in a p-n-junction.

According to another embodiment, it is provided an organic electronic device comprising at least one organic semiconductor layer comprising a compound according to formula 1, wherein the organic semiconductor layer may be arranged between:

a first and a second electrode, in direct contact with the auxiliary ETL, in direct contact with the EML, in direct contact with the ETL, in direct contact with the cathode, or between two emission layers.

According to another embodiment, it is provided an organic electronic device comprising at least one organic semiconductor layer comprising a compound according to formula 1, and comprising at least one anode and at least one cathode, preferably the organic semiconductor layer is arranged between the anode and the cathode.

According to another aspect, it is provided an organic electronic device comprising at least one organic semiconductor layer comprising a compound according to formula 1, wherein the organic electronic device is a lighting device, thin film transistor, a battery, a display device or a photovoltaic cell, preferably a light emitting device.

According to another embodiment, it is provided an organic electronic device comprising at least one organic light emitting device according to any embodiment described throughout this application, preferably, the electronic device comprises the organic light emitting diode in one of embodiments described throughout this application. More preferably, the electronic device is a display device.

The term "organic metal complex" means a compound which comprises one or more metal and one or more organic groups. The metal may be bound to the organic group via a covalent or ionic bond. The organic group means a group comprising mainly covalently bound carbon and hydrogen atoms. The organic group may further comprise heteroatoms selected from N, O, S, B, Si, P, Se, preferably from B, N, O and S.

In the context of the present specification the term "essentially non-emissive" or "non-emitting" means that the visible emission spectrum of the compound or a layer of a) the compound of formula 1 and b) at least one organic metal complex, wherein the metal of the organic metal complex is selected from the group comprising alkali, alkaline earth or rare earth metal in a device is less than 10%, preferably less than 5%, further preferred less than 1%, relative to the visible emission spectrum. The visible emission spectrum is an emission spectrum with a wavelength of about ≥380 nm to about ≤780 nm. Preferably, an organic semiconductor layer or a device comprising a layer, which comprises a) the compound of formula 1 and b) at least one organic metal complex, wherein the metal of the organic metal complex is selected from the group comprising alkali, alkaline earth or rare earth metal, is essentially non-emissive or non-emitting.

The term "free of", "does not contain", "does not comprise" does not exclude impurities which may be present in the compounds prior to deposition. Impurities have no technical effect with respect to the object achieved by the present invention.

The operating voltage, also named U, is measured in Volt (V) at 10 milliAmpere per square centimeter (mA/cm2).

The candela per Ampere efficiency, also named cd/A efficiency, is measured in candela per ampere at 10 milliAmpere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The rate onset temperature is measured in ° C. and describes the VTE source temperature at which measurable evaporation of a compound commences at a pressure of less than $10^{-5}$ mbar.

The term "OLED", "organic light emitting diode", "organic light emitting device", "organic optoelectronic device" and "organic light-emitting diode" are simultaneously used and have the same meaning.

The term "transition metal" means and comprises any element in the d-block of the periodic table, which comprises groups 3 to 12 elements on the periodic table.

The term "group III to VI metal" means and comprises any metal in groups III to VI of the periodic table.

As used herein, "weight percent", "wt.-%", "percent by weight", "% by weight", and variations thereof refer to a compound, composition, component, substance or agent as the weight of that compound, composition, component, substance or agent of the respective electron transport layer divided by the total weight of the composition thereof and multiplied by 100. It is understood that the total weight percent amount of all components, substances or agents of the respective electron transport layer are selected such that it does not exceed 100 wt.-%.

As used herein, "volume percent", "vol.-%", "percent by volume", "% by volume", and variations thereof refer to an elemental metal, a composition, component, substance or agent as the volume of that elemental metal, component, substance or agent of the respective electron transport layer divided by the total volume of the respective electron transport layer thereof and multiplied by 100. It is understood that the total volume percent amount of all elemental metal, components, substances or agents of the respective cathode electrode layer are selected such that it does not exceed 100 vol.-%.

All numeric values are herein assumed to be modified by the term "about", whether or not explicitly indicated. As used herein, the term "about" refers to variation in the numerical quantity that can occur.

Whether or not modified by the term "about", the claims include equivalents to the quantities.

It should be noted that, as used in this specification and the appended claims, the singular forms "a", "an", and "the" include plural referents unless the content clearly dictates otherwise.

It should be noted that, as used in this specification and the appended claims, "*" if not otherwise defined indicates the chemical bonding position.

The anode electrode and cathode electrode may be described as anode electrode/cathode electrode or anode electrode/cathode electrode or anode electrode layer/cathode electrode layer.

In the present specification, when a definition is not otherwise provided, an "alkyl group" may refer to an aliphatic hydrocarbon group. The alkyl group may refer to "a saturated alkyl group" without any double bond or triple bond. The alkyl group may be a linear, cyclic or branched alkyl group.

The alkyl group may be a $C_1$ to $C_{16}$ alkyl group, or preferably a $C_1$ to $C_{12}$ alkyl group. More specifically, the alkyl group may be a $C_1$ to $C_{14}$ alkyl group, or preferably a $C_1$ to $C_{10}$ alkyl group or a $C_1$ to $C_6$ alkyl group. For example, a $C_1$ to $C_4$ alkyl group comprises 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a tert-butyl group, a pentyl group, a hexyl group, a cyclopropyl group, a cyclobutyl group, a cyclopentyl group, a cyclohexyl group, and the like.

In the present specification, "aryl" and "arylene group" may refer to a group comprising at least one hydrocarbon aromatic moiety, and all the elements of the hydrocarbon aromatic moiety may have p-orbitals which form conjugation, for example a phenyl group, a naphthyl group, an anthracenyl group, a phenanthrenyl group, a pyrenyl group, a fluorenyl group and the like.

According to one embodiment, wherein L is a direct bond, phenylene or biphenylene, substituted or unsubstituted $C_6$ to $C_{18}$ arylene, substituted or unsubstituted $C_3$ to $C_{20}$ heteroarylene, or $C_6$ to $C_{40}$ alkenyl, wherein the substituted or unsubstituted $C_6$ to $C_{18}$ arylene is selected from the group comprising a phenylene group, a naphthylene group, an anthracenylene group, a phenanthrenylene group, a pyrenylene group, a fluorenylene group; and wherein the substituents of the substituted $C_6$ to $C_{18}$ arylene and substituted $C_3$ to $C_{20}$ heteroarylene are independently selected from $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, and —$PY(R^2)_2$ with Y being O or S.

The term "heteroaryl" and "heteroarylene" may refer to aromatic heterocycles with at least one heteroatom, and all the elements of the aromatic heterocycle may have p-orbitals which form conjugation, for example a pyridyl, pyrimidyl, pyrazinyl, triazinyl, pyrrolyl, carbazolyl, furanyl, benzofuranyl, dibenzofuranyl, thiophenyl, benzothiophenyl, dibenzothiophenyl group and the like. Preferably, the aromatic heterocycles are free of $sp^3$-hybridised carbon atoms.

The term "substituted or unsubstituted heteroaryl", "substituted or unsubstituted $C_5$ to $C_{24}$ heteroaryl", "substituted or unsubstituted $C_3$ to $C_{24}$ heteroaryl", "substituted or unsubstituted $C_5$ to $C_{18}$ heteroaryl", "substituted or unsubstituted $C_5$ to $C_{17}$ heteroaryl", "substituted or unsubstituted $C_3$ to $C_{17}$ heteroaryl", "substituted or unsubstituted $C_3$ to $C_{12}$ heteroarylene" and the like means that the substituted or unsubstituted heteroaryl comprises at least one heteroaryl ring; or at least one heteroaryl ring and at least one non-heteroaryl ring; or at least two heteroaryl rings and at least one non-heteroaryl ring; or at least three heteroaryl rings and at least one non-heteroaryl ring; or at least one heteroaryl ring and at least two non-heteroaryl rings. The rings of the substituted or unsubstituted heteroaryl can be a fused.

According to one embodiment, wherein G is independently selected from unsubstituted or substituted $C_6$ to $C_{40}$ aryl or $C_3$ to $C_{42}$ heteroaryl, $C_6$ to $C_{40}$ alkenyl, CN, $PY(R^2)_2$ with Y being O or S, wherein the unsubstituted or substituted $C_6$ to $C_{40}$ aryl is selected from the group comprising a phenyl group, a naphthyl group, an anthracenyl group, a phenanthrenyl group, a pyrenyl group, a fluorenyl group, phenyl substituted naphthalene, 1-phenyl naphthalene, benzonitrile substituted naphthalene, fused ring system of at least two to four rings, fused ring system of a central five member ring with three annulated phenyl rings thereto, and wherein the unsubstituted or substituted $C_3$ to $C_{42}$ heteroaryl is selected from a triazine, phenyl substituted triazine, diphenyl substituted triazine, dibenzofurane substituted triazine, a triazine substituted with a phenyl and dibenzofurane, wherein the substituents of the substituted $C_6$ to $C_{18}$ aryl and of the substituted $C_3$ to $C_{20}$ heteroaryl are independently selected from H, CN, F, deuterium, $C_6$ to $C_{18}$ aryl, $C_3$ to $C_{20}$ heteroaryl, $C_1$ to $C_{16}$ alkyl, $C_1$ to $C_{16}$ alkoxy, nitrile, and $PY(R^2)_2$ with Y being O or S;

The term "hetero-fluorene group" refers to a compound comprising the structure of formula 1 wherein at least one of X1 to X8 is N thus constituting a heteroarylene ring.

A heteroarylene ring may comprise at least 1 to 3 heteroatoms. Preferably a heteroarylene ring may comprise at least 1 to 3 heteroatoms individually selected from N, S and/or O.

The compound of formula 1 may comprise at least one heteroaryl/ene ring having at least 1 to 3 N-atoms, or at least 1 to 2-N atoms or at least one N-atom.

Further preferred the compound of formula 1 may comprise at least one heteroaryl/ene ring may having at least 1 to 3 O-atoms, or at least 1 to 2 O-atoms or at least one O-atom.

the compound of formula 1 may comprise at least one heteroaryl/ene ring may having at least 1 to 3 S-atoms, or at least 1 to 2 S-atoms or at least one S-atom.

According to another preferred embodiment the compound according to formula 1 may comprise:

at least 6 to 15 aromatic rings, preferably at least 7 to 12 aromatic rings, further preferred at least 8 to 11 aromatic rings, in addition preferred at least 9 to 11 aromatic rings and also preferred at least 8 to 12 aromatic rings; wherein at least 1 to 5, preferably 3 to 4 or 1 to 2 or 1 are heteroaromatic rings.

According to one embodiment the compound according to formula 1:

comprises at least about 6 to 15 aromatic rings, preferably at least 7 to 12 aromatic rings, further preferred at least 8 to 11 aromatic rings, in addition preferred at least 9 to 11 aromatic rings and also preferred at least 8 to 12 aromatic rings, wherein at least about 1 to about 4, preferably about 1 to about 3 or about 1 to about 2, are hetero aromatic rings, wherein the hetero atoms can be selected from N, O, S.

According to one embodiment the compound according to formula 1 comprises at least one to two fluorene groups, wherein at least one is a hetero-fluorene group.

According to one embodiment the compound according to formula 1 comprises at least one to two fluorene groups, wherein the fluorene groups is/are hetero-fluorene groups.

According to one embodiment the compound according to formula 1 comprises at least one spiro-group.

According to one embodiment the compound according to formula 1 comprises at least two spiro-groups.

According to a further preferred embodiment the compound of formula 1 comprises at least 1 to 5, preferably 2 to 4, or 1 to 3 hetero aromatic rings.

According to a further preferred embodiment the compound of formula 1 comprises at least 1 to 5, preferably 2 to 4, or 1 to 3 hetero aromatic rings, wherein at least one of the aromatic rings is a five member hetero aromatic ring.

According to a further preferred embodiment the compound of formula 1 comprises at least 1 to 5, preferably 2 to 4, or 1 to 3 hetero aromatic rings hetero aromatic rings, wherein at least two of the hetero aromatic rings are five member hetero-aromatic-rings.

According to one embodiment the compound according to formula 1 may comprise at least 6 to 12 non-hetero aromatic rings and 2 to 3 hetero aromatic rings.

According to one preferred embodiment the compound according to formula 1 may comprise at least 7 to 12 non-hetero aromatic rings and 2 to 5 hetero aromatic rings.

According to one preferred embodiment the compound according to formula 1 may comprise at least 7 to 10 non-hetero aromatic rings and 1 to 3 hetero aromatic rings.

Melting Point

The melting point (mp) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 μL Mettler Toledo aluminum pan with lid, a <1 mm hole is pierced into the lid).

According to another embodiment the compound of formula 1 may have a melting point of about ≥250° C. and about ≤400° C., preferably about ≥260° C. and about ≤400° C., further preferred about ≥265° C. and about ≤390° C.

Glass Transition Temperature

The glass transition temperature is measured under nitrogen and using a heating rate of 10 K per min in a Mettler Toledo DSC 822e differential scanning calorimeter as described in DIN EN ISO 11357, published in March 2010.

According to another embodiment the compound of formula 1 may have a glass transition temperature Tg of about ≥124° C. and about ≤3500° C., preferably about ≥130° C. and about ≤300° C.

Rate Onset Temperature

The rate onset temperature is determined by loading 100 mg compound into a VTE source. As VTE source a point source for organic materials is used as supplied by Kurt J. Lesker Company (www.lesker.com) or CreaPhys GmbH (http://www.creaphys.com). The VTE source is heated at a constant rate of 15 K/min at a pressure of less than $10^{-5}$ mbar and the temperature inside the source measured with a thermocouple. Evaporation of the compound is detected with a QCM detector which detects deposition of the compound on the quartz crystal of the detector. The deposition rate on the quartz crystal is measured in Angstrom per second. To determine the rate onset temperature, the deposition rate is plotted against the VTE source temperature. The rate onset is the temperature at which noticeable deposition on the QCM detector occurs. For accurate results, the VTE source is heated and cooled three time and only results from the second and third run are used to determine the rate onset temperature.

To achieve good control over the evaporation rate of an organic compound, the rate onset temperature may be in the range of 200 to 300° C. If the rate onset temperature is below 200° C. the evaporation may be too rapid and therefore difficult to control. If the rate onset temperature is above 300° C. the evaporation rate may be too low which may result in low tact time and decomposition of the organic compound in VTE source may occur due to prolonged exposure to elevated temperatures.

The rate onset temperature is an indirect measure of the volatility of a compound. The higher the rate onset temperature the lower is the volatility of a compound.

According to another embodiment the compound of formula 1 may have a rate onset temperature $T_{RO}$ of about ≥200° C. and about ≤3000° C., preferably about ≥220° C. and about ≤2900° C., further preferred about ≥220° C. and about ≤280° C.

Reduction Potential

The reduction potential is determined by cyclic voltammetry with potentiostatic device Metrohm PGSTAT30 and software Metrohm Autolab GPES at room temperature. The redox potentials given at particular compounds were measured in an argon de-aerated, dry 0.1M THE solution of the tested substance, under argon atmosphere, with 0.1M tetrabutyl-ammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard Fc+/Fc redox couple, afforded finally the values reported above. All studied compounds as well as the reported comparative compounds showed well-defined reversible electrochemical behavior.

Dipole Moment

The dipole moment $|\vec{\mu}|$ of a molecule containing N atoms is given by:

$$\vec{\mu} = \sum_{i}^{N} q_i \vec{r_i}$$

$$|\vec{\mu}| = \sqrt{\mu_x^2 + \mu_y^2 + \mu_z^2}$$

where $q_i$ and $\vec{r_i}$ are the partial charge and position of atom i in the molecule.

The dipole moment is determined by a semi-empirical molecular orbital method. The geometries of the molecular structures are optimized using the hybrid functional B3LYP with the 6-31G* basis set in the gas phase as implemented in the program package TURBOMOLE V6.5 (TURBOMOLE GmbH, Litzenhardtstrasse 19, 76135 Karlsruhe, Germany). If more than one conformation is viable, the conformation with the lowest total energy is selected to determine the bond lengths of the molecules.

According to one embodiment the compounds according to formula 1 may have a dipole moment (Debye) in the range from about ≥0.6 to about ≤8.0, preferably from about ≥1.0.8 to about ≤6.0, further preferred from about ≥0.8 to about ≤6.0.

Calculated HOMO and LUMO

The HOMO and LUMO are calculated with the program package TURBOMOLE V6.5. The optimized geometries and the HOMO and LUMO energy levels of the molecular structures are determined by applying the hybrid functional B3LYP with a 6-31G* basis set in the gas phase. If more than one conformation is viable, the conformation with the lowest total energy is selected.

According to one embodiment the compounds according to formula 1 may have a LUMO energy level (eV) in the range from about −2.50 eV to about −1.50 eV, preferably from about −2.30 eV to about −1.30 eV, further preferred from about −2.20 eV to about −1.30 eV.

Technical Effect

Surprisingly, it was found that the compound according to the invention, an organic semiconductor layer comprising the compound according to the invention and the inventive organic electronic devices solve the problem underlying the present invention by being superior over the organic electroluminescent devices, compounds and compositions known in the art, in particular with respect to lifetime. At the same time the operating voltage is kept at a similar or even improved level which is important for reducing power consumption and increasing battery life, for example of a mobile display device. Long lifetime at high current density is important for the longevity of a device which is run at high brightness.

Additionally, it was surprisingly found that the calculated LUMO level of compounds of formula 1 is significantly more negative than the LUMO of the state of the art. A more negative LUMO may be beneficial for improved electron transfer from the cathode to the emission layer.

Furthermore, it was surprisingly found that the rate onset temperature of compounds of formula 1 is significantly lower than of the state of the art. A lower rate onset temperature may be beneficial for mass production as the deposition rate can be increased without increasing decomposition of the compound in the VTE source.

The inventors have surprisingly found that particular good performance can be achieved when using the organic electroluminescent device as a fluorescent blue device.

The specific arrangements mentioned herein as preferred were found to be particularly advantageous.

Likewise, some compounds falling within the scope of the broadest definition of the present invention have surprisingly be found to be particularly well performing with respect to the mentioned property of cd/A efficiency and/or lifetime. These compounds are discussed herein to be particularly preferred.

Further an organic optoelectronic device having high efficiency and/or long lifetime may be realized.

Anode

A material for the anode may be a metal or a metal oxide, or an organic material, preferably a material with work function above about 4.8 eV, more preferably above about 5.1 eV, most preferably above about 5.3 eV. Preferred metals are noble metals like Pt, Au or Ag, preferred metal oxides are transparent metal oxides like ITO or IZO which may be advantageously used in bottom-emitting OLEDs having a reflective cathode.

In devices comprising a transparent metal oxide anode or a reflective metal anode, the anode may have a thickness from about 50 nm to about 100 nm, whereas semitransparent metal anodes may be as thin as from about 5 nm to about 15 nm, and non-transparent metal anodes may have a thickness from about 15 nm to about 150 nm.

Hole Injection Layer (HIL)

The hole injection layer may improve interface properties between the anode and an organic material used for the hole transport layer, and is applied on a non-planarized anode and thus may planarize the surface of the anode. For example, the hole injection layer may include a material having a median value of the energy level of its highest occupied molecular orbital (HOMO) between the work function of the anode material and the energy level of the HOMO of the hole transport layer, in order to adjust a difference between the work function of the anode and the energy level of the HOMO of the hole transport layer.

When the hole transport region comprises a hole injection layer 36, the hole injection layer may be formed on the anode by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-6}$ Pa to about $10^{-1}$ Pa, and a deposition rate of about 0.1 to about 10 nm/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

The hole injection layer may further comprise a p-dopant to improve conductivity and/or hole injection from the anode.

p-Dopant

In another aspect, the p-dopant may be homogeneously dispersed in the hole injection layer.

In another aspect, the p-dopant may be present in the hole injection layer in a higher concentration closer to the anode and in a lower concentration closer to the cathode.

The p-dopant may be one of a quinone derivative or a radialene compound but not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), 4,4',4"-((1E,1'E,1"E)-cyclopropane-1,2,3-triylidenetris(cyanomethanylylidene))-tris(2,3,5,6-tetrafluorobenzonitrile).

According to another embodiment, an organic electronic device comprising an organic semiconductor layer comprising a compound according to invention may additional comprise a layer comprising a radialene compound and/or a quinodimethane compound.

In another embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment, the radialene and/or the quinodimethane compound may be comprised in a hole injection, hole transporting and/or a hole generation layer.

In one embodiment, the radialene compound may have formula (XX) and/or the quinodimethane compound may have formula (XXIa) or (XXIb):

(XX)

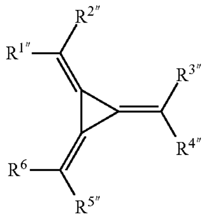

(XXIa)

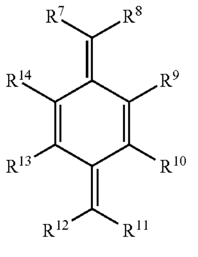

(XXIb)

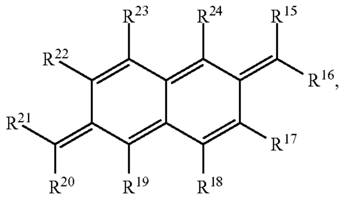

wherein $R^{1''}$, $R^{2''}$, $R^{3''}$, $R^{4''}$, $R^{5''}$, $R^6$, $R^7$, $R^8$, $R^{11}$, $R^{12}$, $R^{15}$, $R^{16}$, $R^{20}$, $R^{21}$ are independently selected from an electron withdrawing groups and $R^9$, $R^{10}$, $R^{13}$, $R^{14}$, $R^{17}$, $R^{18}$, $R^{19}$, $R^{22}$, $R^{23}$ and $R^{24}$ are independently selected from H, halogen and electron withdrawing groups. Electron withdrawing group/s that can be suitable used are above mentioned.

Hole Transport Layer (HTL)

Conditions for forming the hole transport layer and the electron blocking layer may be defined based on the above-described formation conditions for the hole injection layer.

A thickness of the hole transport part of the charge transport region may be from about 10 nm to about 1000 nm, for example, about 10 nm to about 100 nm. When the hole transport part of the charge transport region comprises the hole injection layer and the hole transport layer, a thickness of the hole injection layer may be from about 10 nm to about 1000 nm, for example about 10 nm to about 100 nm and a thickness of the hole transport layer may be from about 5 nm to about 200 nm, for example about 10 nm to about 150 nm. When the thicknesses of the hole transport part of the charge transport region, the HIL, and the HTL are within these ranges, satisfactory hole transport characteristics may be obtained without a substantial increase in operating voltage.

Hole transport matrix materials used in the hole transport region are not particularly limited. Preferred are covalent compounds comprising a conjugated system of at least 6 delocalized electrons, preferably organic compounds comprising at least one aromatic ring, more preferably organic compounds comprising at least two aromatic rings, even more preferably organic compounds comprising at least three aromatic rings, most preferably organic compounds comprising at least four aromatic rings. Typical examples of hole transport matrix materials which are widely used in hole transport layers are polycyclic aromatic hydrocarbons, triarylene amine compounds and heterocyclic aromatic compounds. Suitable ranges of frontier orbital energy levels of hole transport matrices useful in various layer of the hole transport region are well-known. In terms of the redox potential of the redox couple HTL matrix/cation radical of the HTL matrix, the preferred values (if measured for example by cyclic voltammetry against ferrocene/ferrocenium redox couple as reference) may be in the range 0.0-1.0 V, more preferably in the range 0.2-0.7 V, even more preferably in the range 0.3-0.5 V.

Buffer Layer

The hole transport part of the charge transport region may further include a buffer layer.

Buffer layer that can be suitable used are disclosed in U.S. Pat. Nos. 6,140,763, 6,614,176 and in US2016/248022.

The buffer layer may compensate for an optical resonance distance of light according to a wavelength of the light emitted from the EML, and thus may increase efficiency.

Emission Layer (EML)

The emission layer may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include an emitter host (EML host) and an emitter dopant (further only emitter).

A thickness of the emission layer may be about 100 Å to about 1000 Å, for example about 200 Å to about 600 Å. When the thickness of the emission layer is within these ranges, the emission layer may have improved emission characteristics without a substantial increase in operating voltage.

Emitter Host

According to another embodiment, the emission layer comprises compound of formula 1 as emitter host.

The emitter host compound has at least three aromatic rings, which are independently selected from carbocyclic rings and heterocyclic rings.

Other compounds that can be used as the emitter host is an anthracene matrix compound represented by formula 400 below:

Formula 400

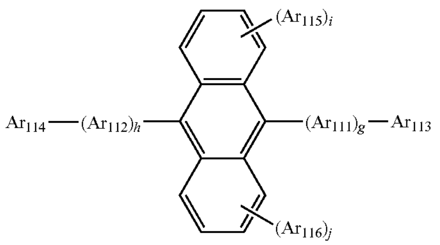

In formula 400, $Ar_{111}$ and $Ar_{112}$ may be each independently a substituted or unsubstituted $C_6$-$C_{60}$ arylene group; $Ar_{113}$ to $Ar_{116}$ may be each independently a substituted or unsubstituted $C_1$-$C_{10}$ alkyl group or a substituted or unsubstituted $C_6$-$C_{60}$ arylene group; and g, h, i, and j may be each independently an integer from 0 to 4.

In some embodiments, $Ar_{111}$ and $Ar_{112}$ in formula 400 may be each independently one of a phenylene group, a naphthalene group, a phenanthrenylene group, or a pyrenylene group; or a phenylene group, a naphthalene group, a phenanthrenylene group, a fluorenyl group, or a pyrenylene group, each substituted with at least one of a phenyl group, a naphthyl group, or an anthryl group.

In formula 400, g, h, i, and j may be each independently an integer of 0, 1, or 2.

In formula 400, $Ar_{113}$ to $Ar_{116}$ may be each independently one of a $C_1$-$C_{10}$ alkyl group substituted with at least one of a phenyl group, a naphthyl group, or an anthryl group;

a phenyl group, a naphthyl group, an anthryl group, a pyrenyl group, a phenanthrenyl group, or a fluorenyl group;

a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group

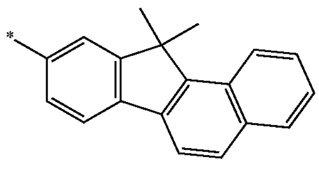

;

or formulas 10 or 11

(7)

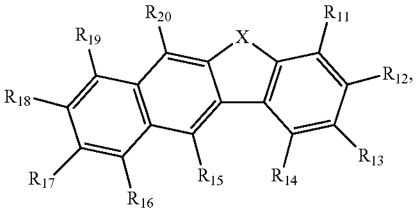

(8)

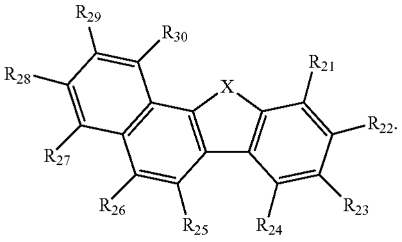

Wherein in the formulas 10 and 11, X is selected form an oxygen atom and a sulfur atom, but embodiments of the invention are not limited thereto.

In the formula 10, any one of $R_{11}$ to $R_{14}$ is used for bonding to $Ar_{111}$, $R_{11}$ to $R_{14}$ that are not used for bonding to $Ar_{111}$ and $R_{15}$ to $R_{20}$ are the same as $R_1$ to $R_8$.

In the formula 11, any one of $R_{21}$ to $R_{24}$ is used for bonding to $Ar_{111}$, $R_{21}$ to $R_{24}$ that are not used for bonding to $Ar_{111}$ and $R_{25}$ to $R_{30}$ are the same as $R_1$ to $R_8$.

Preferably, the EML host comprises between one and three heteroatoms selected from the group consisting of N, O or S. More preferred the EML host comprises one heteroatom selected from S or O.

Emitter Dopant

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The emitter may be a red, green, or blue emitter.

The dopant may be a fluorescent dopant, for example ter-fluorene, the structures are shown below. 4.4'-bis(4-diphenyl amiostyryl)biphenyl (DPAVBI, 2,5,8,11-tetra-tert-butyl perylene (TBPe), and Compound 12 below are examples of fluorescent blue dopants.

Compound 12

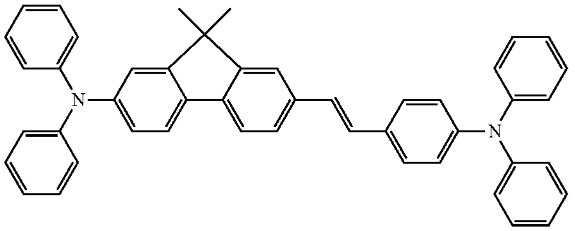

The dopant may be a phosphorescent dopant, and examples of the phosphorescent dopant may be an organic metal compound comprising Ir, Pt, Os, Ti, Zr, Hf, Eu, Tb, Tm, Fe, Co, Ni, Ru, Rh, Pd, or a combination thereof. The phosphorescent dopant may be, for example a compound represented by formula Z, but is not limited thereto:

$$J_2MX \quad (Z).$$

In formula Z, M is a metal, and J and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the J and X may be, for example a bidendate ligand.

One or more emission layers may be arranged between the anode and the cathode. To increase overall performance, two or more emission layers may be present.

Charge Generation Layer

A charge generation layer (also named CGL) may be arranged between the first and the second emission layer, and second and third emission layer, if present. Typically, the CGL comprises a n-type charge generation layer (also named n-CGL or electron generation layer) and a p-type charge generation layer (also named p-CGL or hole generation layer). An interlayer may be arranged between the n-type CGL and the p-type CGL.

In an embodiment the CGL may comprise the compound of formula (1). In one aspect, the n-type CGL may comprise a matrix compound and a metal, metal salt or organic metal complex, preferably a metal. The metal may be selected from an alkali, alkaline earth or rare earth metal. The organic semiconductor layer comprising the compound according to the invention may be arranged between the first emission layer and the n-CGL and/or between the second and/or third emission layer and the cathode.

The p-type CGL may comprise a dipyrazino[2,3-f:2',3'-h]quinoxaline, a quinone compound or a radialene compound, preferably dipyrazino[2,3-f:2',3'-h]quinoxaline-2,3,6,7,10,11-hexacarbonitrile or a compound or formula (XX) and/or a compound of formula (XXIa) or (XXIb).

Electron Transport Layer (ETL)

According to another embodiment, the organic semiconductor layer that comprises the compound according to the invention is an electron transport layer. In another embodiment the electron transport layer may consist of the compound according to the invention.

In another embodiment, the organic electronic device comprises an electron transport region of a stack of organic layers formed by two or more electron transport layers, wherein at least one electron transport layer comprises the compound according to the invention.

In an embodiment it may be provided that the electron transport layer does not contain a dopant or an additive.

Alternatively, the electron transport layer may comprise an n-type additive which may be selected from a metal, a metal salt or a metal complex. The n-type additive may be an n-type dopant. The n-type dopant may be a reductive dopant in the sense that it donates an electron to the matrix material of the ETL. In this regard, the metal may be selected from alkali metal, alkaline earth metal and transition metal which may be a rare earth metal. The metal salt may be the salt of an alkali metal, the salt of an alkaline earth metal or the salt of a rare earth metal. The alkali metal salt may be selected from the group consisting of LiF, LiCl, LiBr or LiI, alternatively may be LiF. The metal complex may be an organic alkali metal complex, alternatively an alkali metal complex, alternatively LiQ or alkali borate.

The electron transport layer may include one or two or more different compounds of formula (1).

The electron transport layer may include one or two or more different compounds of formula (1) and a metal salt.

The electron transport layer may include one or two or more different compounds of formula (1) and an organic metal complexes.

The thickness of the electron transport layer may be from about 0.5 nm to about 100 nm, for example about 2 nm to about 40 nm. When the thickness of the electron transport layer is within these ranges, the electron transport layer may have improved electron transport ability without a substantial increase in operating voltage.

Electron Injection Layer (EIL)

According to another aspect of the invention, the organic electroluminescent device may further comprise an electron injection layer between the electron transport layer (first-ETL) and the cathode.

The electron injection layer (EIL) may facilitate injection of electrons from the cathode.

According to another aspect of the invention, the electron injection layer comprises:

(i) an electropositive metal selected from alkali metals, alkaline earth metals and rare earth metals in substantially elemental form, preferably selected from Li, Na, K, Rb, Cs, Mg, Ca, Sr, Ba, Eu and Yb, more preferably from Li, Na, Mg, Ca, Sr and Yb, even more preferably from Li and Yb, most preferably Yb; and/or (ii) an alkali metal complex and/or alkali metal salt, preferably the Li complex and/or salt, more preferably a Li quinolinolate, even more preferably a lithium 8-hydroxyquinolinolate, most preferably the alkali metal salt and/or complex of the second electron transport layer (second-ETL) is identical with the alkali metal salt and/or complex of the injection layer.

The electron injection layer may include at least one selected from LiF, NaCl, CsF, $Li_2O$, and BaO.

A thickness of the EIL may be from about 0.1 nm to about 10 nm, or about 0.3 nm to about 9 nm. When the thickness of the electron injection layer is within these ranges, the electron injection layer may have satisfactory electron injection ability without a substantial increase in operating voltage.

The electron injection layer may comprise or consist of the compound according to the invention.

Cathode

A material for the cathode may be a metal, an alloy, or an electrically conductive compound that have a low work function, or a combination thereof. Specific examples of the material for the cathode may be lithium (Li), magnesium (Mg), aluminum (Al), aluminum-lithium (Al—Li), calcium (Ca), magnesium-indium (Mg—In), magnesium-silver (Mg—Ag), silver (Ag) etc. In order to manufacture a top-emission light-emitting device having a reflective anode deposited on a substrate, the cathode may be formed as a light-transmissive electrode from, for example, indium tin oxide (ITO), indium zinc oxide (IZO) or silver (Ag).

In devices comprising a transparent metal oxide cathode or a reflective metal cathode, the cathode may have a thickness from about 50 nm to about 100 nm, whereas semitransparent metal cathodes may be as thin as from about 5 nm to about 15 nm.

Substrate

A substrate may be further disposed under the anode or on the cathode. The substrate may be a substrate that is used in a general organic light emitting diode and may be a glass substrate or a transparent plastic substrate with strong mechanical strength, thermal stability, transparency, surface smoothness, ease of handling, and water resistance.

Hereinafter, the embodiments are illustrated in more detail with reference to examples. However, the present disclosure is not limited to the following examples.

DESCRIPTION OF THE DRAWINGS

These and/or other aspects and advantages of the present invention will become apparent and more readily appreciated from the following description of the exemplary embodiments, taken in conjunction with the accompanying drawings, of which.

Figure 1:
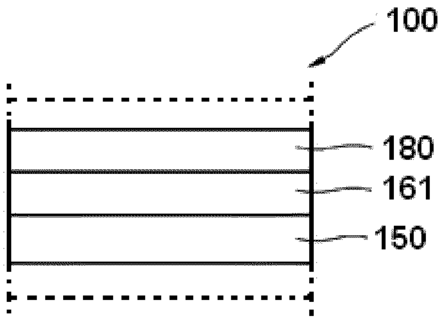
FIG. 1 is a schematic sectional view of an organic light-emitting diode (OLED), according to an exemplary embodiment of the present invention with an emission layer, one electron transport layer and an electron injection layer.

Reference will now be made in detail to the exemplary aspects, examples of which are illustrated in the accompanying drawings, wherein like reference numerals refer to the like elements throughout. The exemplary embodiments are described below, in order to explain the aspects, by referring to the figures.

Herein, when a first element is referred to as being formed or disposed "on" a second element, the first element can be disposed directly on the second element, or one or more other elements may be disposed there between. When a first element is referred to as being formed or disposed "directly on" a second element, no other elements are disposed there between.

The term "contacting sandwiched" refers to an arrangement of three layers whereby the layer in the middle is in direct contact with the two adjacent layers.

The organic light emitting diodes according to an embodiment of the present invention may include a hole transport region; an emission layer; and a first electron transport layer comprising the compound according to the invention.

FIG. 1 is a schematic sectional view of an organic light-emitting diode 100, according to an exemplary embodiment of the present invention. The OLED 100 comprises an emission layer 150, an electron transport layer (ETL) 161 comprising the compound according to the invention, and an electron injection layer 180, whereby the first electron transport layer 161 is disposed directly on the emission layer 150 and the electron injection layer 180 is disposed directly on the first electron transport layer 161.

Figure 2:
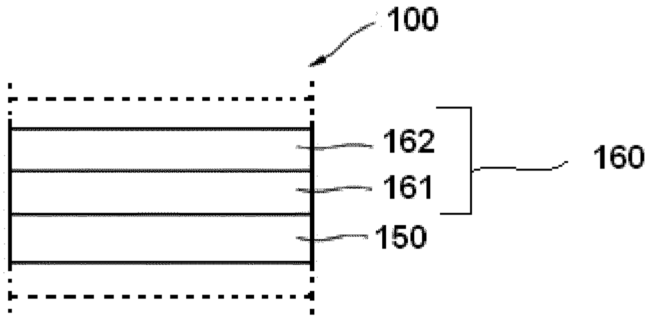
FIG. 2 is a schematic sectional view of an organic light-emitting diode (OLED), according to an exemplary embodiment of the present invention with an emission layer and two electron transport layers.

FIG. 2 is a schematic sectional view of an organic light-emitting diode 100, according to an exemplary embodiment of the present invention. The OLED 100 comprises an emission layer 150 and an electron transport layer stack (ETL) 160 comprising a first electron transport layer 161, and a second electron transport layer 162 comprising the compound according to the invention, whereby the second electron transport layer 162 is disposed directly on the first electron transport layer 161.

Figure 3:
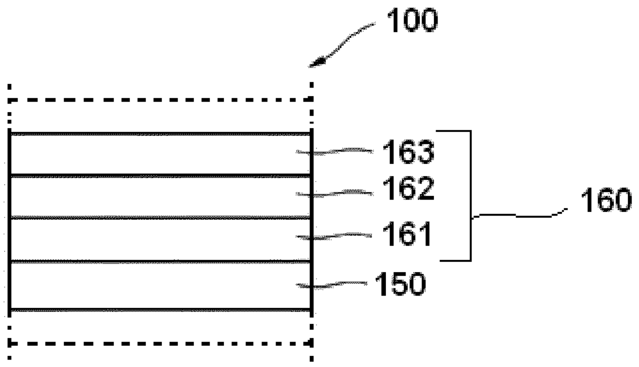
FIG. 3 is a schematic sectional view of an OLED, according to an exemplary embodiment of the present invention with an emission layer and three electron transport layers.

FIG. 3 is a schematic sectional view of an organic light-emitting diode 100, according to an exemplary embodiment of the present invention. The OLED 100 comprises an emission layer 150 and an electron transport layer stack (ETL) 160 comprising a first electron transport layer 161, a second electron transport layer 162, and a third electron transport layer 163, whereby the second electron transport layer 162 is disposed directly on the first electron transport layer 161 and the third electron transport layer 163 is disposed directly on the first electron transport layer 162. The first and/or the second and/or the third electron transport layer comprise the compound according to the invention.

Figure 4:
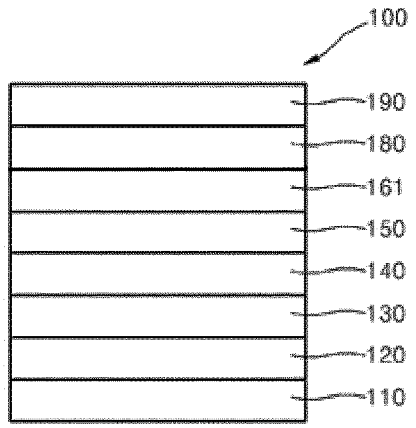
FIG. 4 is a schematic sectional view of an organic light-emitting diode (OLED), according to an exemplary embodiment of the present invention with an emission layer and one electron transport layer.

FIG. 4 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, one first electron transport layer (ETL) 161, an electron injection layer (EIL) 180, and a cathode electrode 190. The first electron transport layer (ETL) 161 comprises the compound according to the invention. The electron transport layer (ETL) 161 is formed directly on the EML 150.

Figure 5:
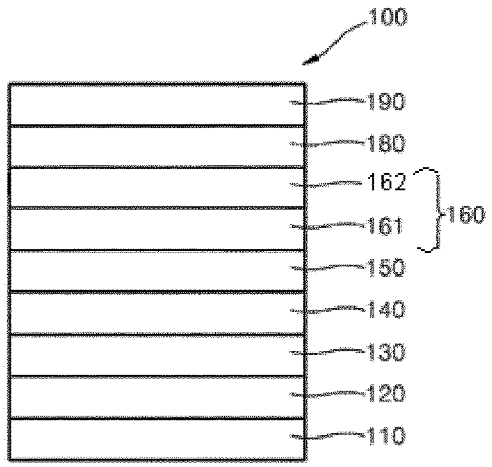
FIG. 5 is a schematic sectional view of an organic light-emitting diode (OLED), according to an exemplary embodiment of the present invention with an emission layer and two electron transport layers.

FIG. 5 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a cathode electrode 190. The electron transport layer (ETL) 160 comprises a first electron transport layer 161 and a second electron transport layer 162, wherein the first electron transport layer is arranged near to the anode (120) and the second electron transport layer is arranged near to the cathode (190). The first and/or the second electron transport layer comprise the compound according to the invention.

Figure 6:
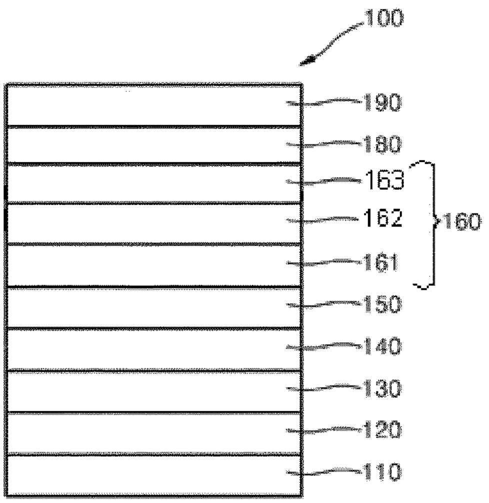
FIG. 6 is a schematic sectional view of an OLED, according to an exemplary embodiment of the present invention with an emission layer and three electron transport layers.

FIG. 6 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a second cathode electrode 190. The electron transport layer stack (ETL) 160 comprises a first electron transport layer 161, a second electron transport layer 162 and a third electron transport layer 163. The first electron transport layer 161 is formed directly on the emission layer (EML) 150. The first, second and/or third electron transport layer comprise the compound according to the invention.

Hereinafter, the embodiments are illustrated in more detail with reference to examples. However, the present disclosure is not limited to the following examples. Reference will now be made in detail to the exemplary aspects.

General Synthetic Scheme of Key Intermediates

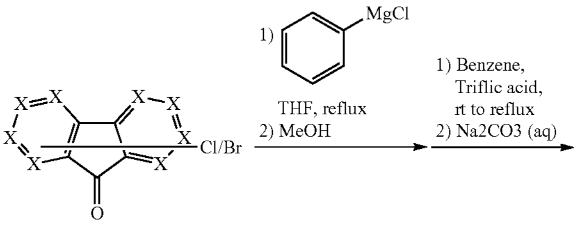

Molecule A

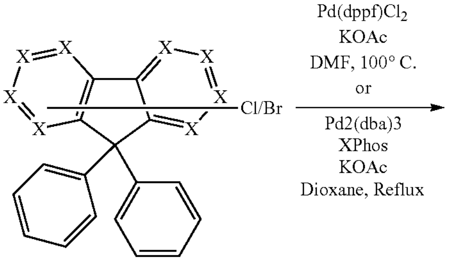

Molecule C

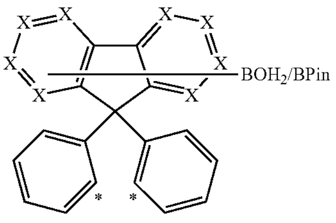

Molecule C'

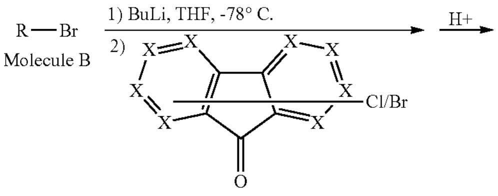

Molecule A

THF, -78° C. to R.T.

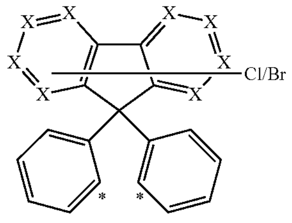

Molecule C

Synthesis of C5.1: 7'-chlorospiro[fluorene-9,5'-indeno[1,2-c]pyridine]

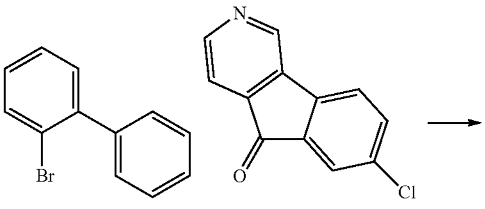

2052-07-5 114995-34-5

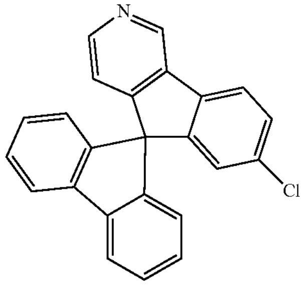

To an anhydrous THE solution (360 ml) containing 2-bromo-1,1'-biphenyl (16.8 g, 72.2 mmol) at −90° C. under inert atmosphere and stirring, n-butyl lithium (30.4 mL, 75.8 mmol, 2.5 M in hexanes) was added slowly, during 30 minutes. After 1h 30 min, a solution of 7-chloro-5H-indeno[1,2-c]pyridin-5-one (14.8 g, 68.6 mmol) in anhydrous THE (400 mL) and under inert atmosphere was added slowly, during an hour. The reaction mixture was allowed to warm to room temperature overnight, and then was quenched by addition of water (200 mL). The product was extracted with dichloromethane (2×250 mL), the organic phase was washed with water (2×250 mL) and $NaCl_{(aq)}$ (50 mL), dried over anhydrous MgSO4, and the solvent was partially evaporated. Precipitation was favored by addition of toluene. The resulting suspension was stirred at room temperature and the precipitate was collected by suction filtration to yield 20.5 g of 5-([1,1'-biphenyl]-2-yl)-7-chloro-5H-indeno[1,2-c]pyridin-5-ol. This intermediate compound was stirred in a mixture of sulfuric acid (5.5 mL) and acetic acid (550 mL) at 120° C. overnight. After cooling down to room temperature, the solution was added slowly to water (500 mL). Additional water (1500 mL) was added and the resulting precipitate was isolated by suction filtration and washed with water (500 mL) to yield 20.6 g (81%) of a beige solid after drying.

Synthesis of C5.2: 7'-chlorospiro[fluorene-9,5'-indeno[1,2-b]pyridine]

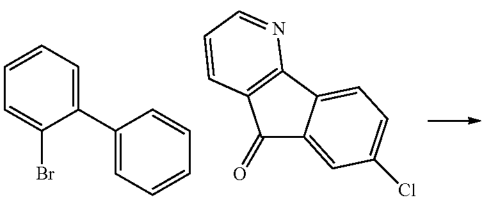

2052-07-5 114995-34-5

-continued

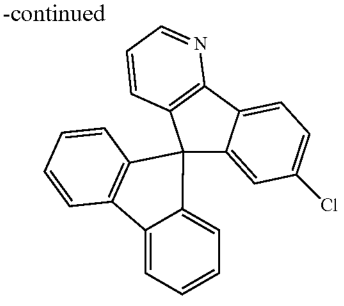

2-Bromo-1,1'-biphenyl (30.0 g, 129.0 mmol) was dissolved in toluene (150 ml). The solvent was evaporated to remove water by azeotropic distillation using a rotary evaporator. After evaporation of the solvent, the starting material was kept for 1 h at 1 mbar and 55° C. A 500 mL 4-necked round-bottom flask (equipped with reflux condenser, thermometer, valve and septum) was dried and kept under nitrogen. The flask was charged with magnesium (3.2 g, 135.1 mmol) and THE (150 ml, dry) was added. In a different dried flask and under nitrogen atmosphere, the pre-dried 2-bromo-1,1'-biphenyl (30 g, 129 mmol) was dissolved in THE (75 mL, dry) and then added to the Magnesium suspension via a syringe. After 1 hour, the reaction mixture was heated up to reflux for 4 hours. Then it was cooled down to room temperature and the Grignard was added on to a solution of 7-chloro-5H-indeno[1,2-b]pyridin-5-one (27.8 g, 129.0 mmol) in THE (230 mL, dry) under nitrogen atmosphere. The mixture was refluxed overnight. After cooling down to room temperature, water was added and the product was extracted with dichloromethane. The organic phase was washed with water until pH neutral and dried over anhydrous $MgSO_4$. Solvent was partially evaporated and the resulting suspension was stirred at room temperature. The precipitate was collected by suction filtration and stirred in dichloromethane (140 mL) for two hours. The precipitate was collected by suction filtration and dried to yield 24.9 g of 5-([1,1'-biphenyl]-2-yl)-7-chloro-5H-indeno[1,2-b]pyridin-5-ol.

This intermediate compound was stirred in a mixture of sulfuric acid (5.3 mL) and acetic acid (666 mL) at 120° C. overnight. After cooling down to room temperature, the solution was added slowly to water (500 mL). Additional water (2000 mL) was added and the resulting precipitate was isolated by suction filtration and washed with water (500 mL) to yield 22.6 g (50%) of a solid after drying.

Synthesis of C'5.2: 7'-(4,4,5,5-tetramethyl-1,3,2-dioxaborolan-2-yl)spiro[fluorene-9,5'-indeno[1,2-b]pyridine]

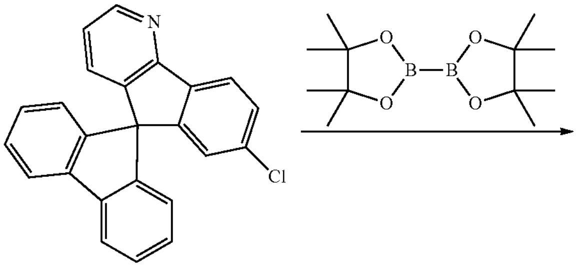

-continued

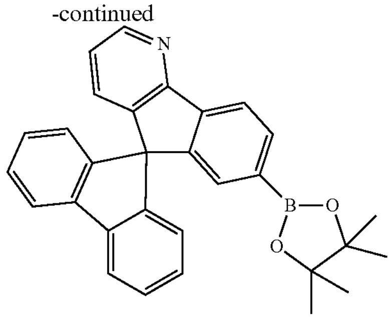

Compound C5.2 (8.0 g, 12.7 mmol), bis(pinacolato)diboron (6.9 g, 27.2 mmol), and potassium acetate (6.7 g, 68.2 mmol) were loaded in a three-neck flask and brought under argon atmosphere, whereupon DMF (100 mL) was added. 2-Dicyclohexylphosphino-2',4',6'-triisopropylbiphenyl (X-Phos, 330 mg, 0.68 mmol) and tris(dibenzylideneacetone)-dipalladium(0) (310 mg, 0.34 mmol) were subsequently added, followed by DMF (130 mL), and the mixture reacted at 110° C. overnight. The mixture was allowed to cool to room temperature and the solvent removed under reduced pressure. The solid residue was dissolved in chloroform (800 mL) and the organic layer washed with water (4x300 mL) until pH neutral. The organic phase was dried over $MgSO_4$, and then filtered over a pad of silica, and the solvent removed under reduced pressure. The solid residue was dissolved in dichloromethane (120 mL), and then the solvent was partially removed under reduced pressure. Methanol was added (220 mL) and the resulting precipitate recovered by suction filtration. The solid was then re-dissolved in dichloromethane, and precipitated using hexane. The resulting precipitate was recovered by suction filtration, washed with methanol (3x10 mL), and dried under vacuum to yield 6.8 g (67%) of a white solid. m/z=444 ($[M+H]^+$).

General Synthetic Scheme of Final Compound from Key Intermediates

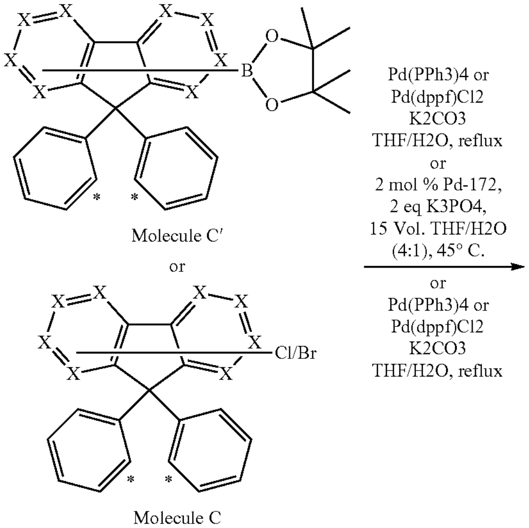

Molecule C′ or

Molecule C

Compound of Formula 1

Synthesis of Final Compounds

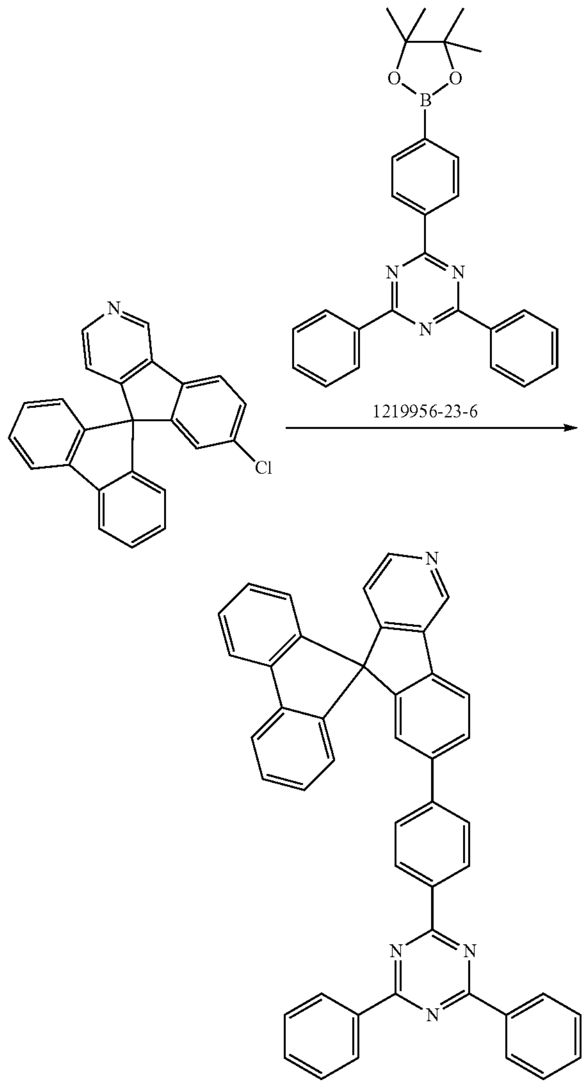

7'-(4-(4,6-diphenyl-1,3,5-triazin-2-yl)phenyl)spiro[fluorene-9,5'-indeno[1,2-c]pyridine]-Compound A-1

A flask was flushed with nitrogen and charged with 7'-chlorospiro[fluorene-9,5'-indeno[1,2-c]pyridine] (9.0 g, 25.6 mmol), 2,4-diphenyl-6-(4-(4,4,5,5-tetramethyl-1,3,2-dioxaborolan-2-yl)phenyl)-1,3,5-triazine (11.3 g, 25.6 mmol), chloro(crotyl)(2-dicyclohexylphosphino-2',6'-dimethoxybiphenyl)palladium(II) (310 mg, 0.51 mmol), potassium phosphate (13.9 g, 64.0 mmol). A mixture of deaerated THF/water (4:1, 160 mL) was added and the reaction mixture was heated to 50° C. under a nitrogen atmosphere overnight. After cooling down to room temperature, the resulting precipitate was isolated by suction filtration and washed with water (3×100 mL). The crude product was then dissolved in toluene and filtered through a silica gel pad. After rinsing with additional toluene (2 L) and chlorobenzene (1 L), the target compound was eluted with dichloromethane/ethylacetate 4/1 (2 L). The filtrate was concentrated under reduced pressure to a minimal volume and n-hexane (200 mL) was added. The resulting suspension was stirred at room temperature and the precipitate was collected by suction filtration to yield 10.5 g (66%) of a solid after drying. Final purification was achieved by sublimation. m/z=625 ([M+H]$^+$).

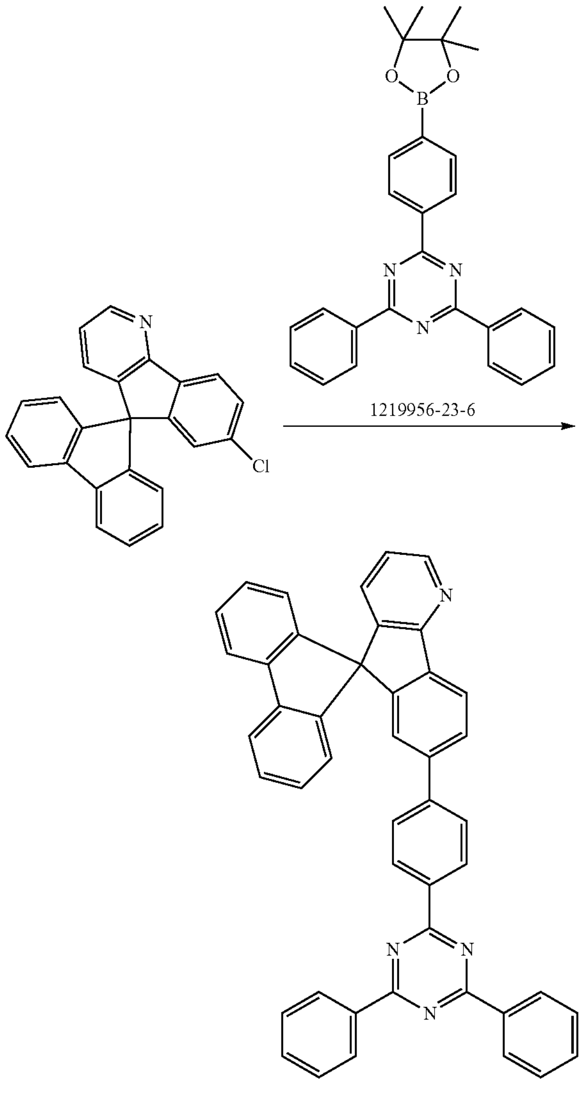

7'-(4-(4,6-diphenyl-1,3,5-triazin-2-yl)phenyl)spiro[fluorene-9,5'-indeno[1,2-b]pyridine]-Compound A-3

A flask was flushed with nitrogen and charged with 7'-chlorospiro[fluorene-9,5'-indeno[1,2-b]pyridine] (6.0 g, 17.0 mmol), 2,4-diphenyl-6-(4-(4,4,5,5-tetramethyl-1,3,2-dioxaborolan-2-yl)phenyl)-1,3,5-triazine (7.4 g, 17.0 mmol), chloro(crotyl)(2-dicyclohexylphosphino-2',6'-dimethoxybiphenyl)palladium(II) (206 mg, 2.0 mol %), potassium phosphate (7.2 g, 34.0 mmol). A mixture of deaerated THF/water (8:1, 112 mL) was added and the reaction mixture was heated to 50° C. under a nitrogen atmosphere overnight. After cooling down to room temperature, the resulting precipitate was isolated by suction filtration and washed with water (3×100 mL). The crude product was then dissolved in toluene and purified by column chromatography, using as eluent first toluene and then toluene/methanol 100/1. The filtrate was concentrated under reduced pressure to a minimal volume and n-hexane (70 mL) was added. The resulting suspension was stirred at room temperature and the precipitate was collected by suction filtration. Finally, it was recrystallized in chlorobenzene to yield 8.0 g (76%) of a solid after drying. Final purification was achieved by sublimation. m/z=625 ([M+H]$^+$).

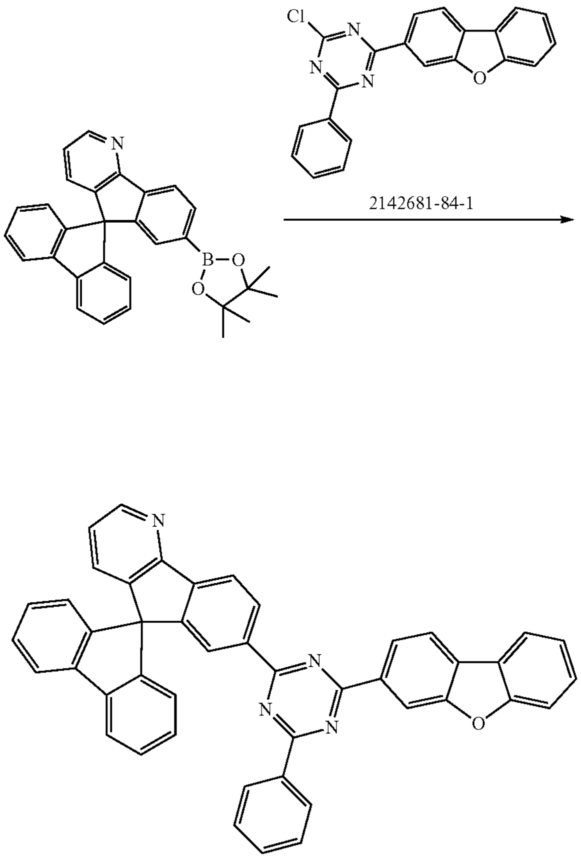

7'-(4-(dibenzo[b,d]furan-3-yl)-6-phenyl-1,3,5-triazin-2-yl)spiro[fluorene-9,5'-indeno[1,2-b]pyridine]—Compound A-2

A flask was charged with a solution of 7'-(4,4,5,5-tetramethyl-1,3,2-dioxaborolan-2-yl)spiro[fluorene-9,5'-indeno[1,2-b]pyridine] (6.7 g, 15.2 mmol) in THE (120 mL), and an aqueous solution (20 mL) of potassium carbonate (4.2 g, 30.4 mmol). The resulting mixture was deaerated by bubbling through $N_2$ gas. [1,1'-Bis(diphenylphosphino)ferrocene]dichloropalladium(II) (220 mg, 3.0 mmol) was then added in a counter flow of $N_2$, and the reaction mixture was reacted at 75° C. for 1 day. The resulting mixture was then allowed to cool to room temperature, further cooled by means of an ice bath, and the resulting precipitate isolated by suction filtration. The crude product was dissolved in hot chlorobenzene (900 mL), and the resulting solution filtered over a silica gel pad. After rinsing with additional hot chlorobenzene (2200 mL), followed by a mixture of hexane (1%, vol.) in chlorobenzene, the organic solvent was removed under reduced pressure. The solid residue was triturated in hot chlorobenzene, and the resulting precipitate was collected by suction filtration, to yield 7.4 g (76%) of a white solid after drying. Final purification was achieved by sublimation. m/z=639 ([M+H]$^+$).

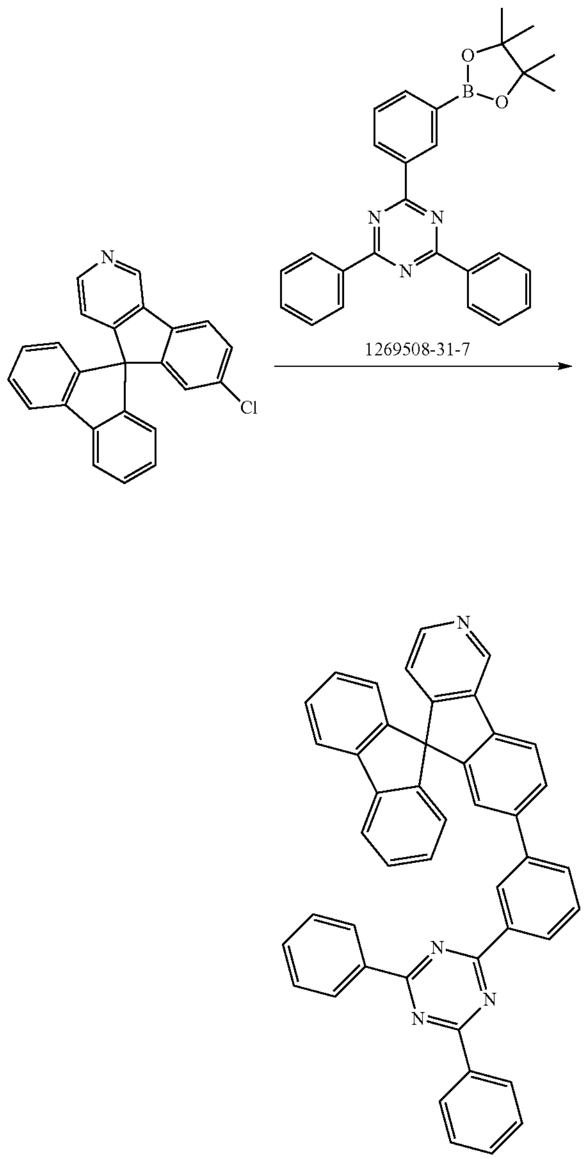

7'-(3-(4,6-diphenyl-1,3,5-triazin-2-yl)phenyl)spiro[fluorene-9,5'-indeno[1,2-c]pyridine]-Compound A-4

A flask was charged with deaerated solutions of 7'-chlorospiro[fluorene-9,5'-indeno[1,2-c]pyridine] (5.5 g, 15.6 mmol) and 2,4-diphenyl-6-(4-(4,4,5,5-tetramethyl-1,3,2-dioxaborolan-2-yl)phenyl)-1,3,5-triazine (6.8 g, 15.6 mmol) in THE (100 mL), and an aqueous solution (40 mL) of potassium phosphate (8.3 g, 39.0 mmol). Chloro(crotyl)(2-dicyclohexylphosphino-2',6'-dimethoxybiphenyl)palladium (II) (190 mg, 2.0 mol %) was subsequently added in a counter flow of $N_2$, and the reaction mixture was reacted at 60° C. overnight. The mixture was allowed to cool to room temperature, the resulting precipitate was isolated by suction filtration, washed with a minimal amount of THF, water (400 mL) until neutral pH, and methanol. The crude product was dissolved in hot chlorobenzene (400 mL), and the resulting solution filtered over a silica gel pad. After rinsing with additional hot chlorobenzene (2500 mL), the resulting solution was concentrated under reduced pressure and the residue triturated overnight at room temperature. The resulted precipitate was recovered by suction filtration, washed with chlorobenzene (100 mL) and hexane, and dried under vacuum to afford 6.7 g (69%) of a white solid. Final purification was achieved by sublimation, m/z=625 ($[M+H]^+$).

US 2015171340. LiQ is commercially available (CAS 25387-93-3). Metal borates may be synthesized as described in WO2013079676A1.

General Procedure for Fabrication of OLEDs

For top emission devices, Examples 1 to 4 and comparative example 1, a glass substrate was cut to a size of 150 mm×150 mm×0.7 mm, was ultrasonically cleaned with a 2% aquatic solution of Deconex FPD 211 for 7 minutes and then with pure water for 5 minutes, and dried for 15 minutes in a spin rinse dryer. Subsequently, Ag was deposited as anode at a pressure of 10-5 to 10-7 mbar.

Then, HT-1 and D-1 were vacuum co-deposited on the anode to form a HIL. Then, HT-1 was vacuum deposited on the HIL, to form an HTL. Then, HT-2 was vacuum deposited on the HTL to form an electron blocking layer (EBL).

Afterwards the emission layer was formed on the EBL by co-deposition of HOST-1 and EMITTER-1.

Then, the ET-1 was vacuum deposited onto the emission layer to form the hole blocking layer (HBL). Then, the electron transport layer was formed on the hole blocking layer by co-depositing a compound of formula (I) and LiQ for examples-1 to -3. For the comparative example the electron transport layer was formed on the hole blocking layer by co-depositing the compound comparative-1 and LiQ.

Then, the electron injection layer is formed on the electron transporting layer by deposing Yb.

Ag:Mg is then evaporated at a rate of 0.01 to 1 Å/s at 10-7 mbar to form a cathode.

A cap layer of HT-1 is formed on the cathode.

The details of the layer stack in the top emission OLED devices are given below. A slash "/" separates individual layers. Layer thicknesses are given in squared brackets [ . . . ], mixing ratios in wt % given in round brackets ( . . . ):

Layer Stack Details

Ag [100 nm]/HT-1:D-1 (92:8) [10 nm]/HT-1 [118 nm]/HT-2 [5 nm]/H09:BD200 (97:3) [20 nm]/ET-1 [5 nm]/Compound of formula (I): LiQ (1:1) [31 nm]/Yb [2 nm]/Ag:Mg (90:10) [13 nm]/HT-1 [70 nm].

TABLE 1

List of compounds used

| | IUPAC name | Reference |
|---|---|---|
| HT-1 | N-([1,1'-biphenyl]-4-yl)-9,9-dimethyl-N-(4-(9-phenyl-9H-carbazol-3-yl)phenyl)-9H-fluoren-2-amine [CAS 1242056-42-3] | US2016322581 |
| HT-2 | N,N-bis(4-(dibenzo[b,d]furan-4-yl)phenyl)-[1,1':4',1''-terphenyl]-4-amine [CAS 1198399-61-9] | JP2014096418 |

TABLE 1-continued

List of compounds used

| | IUPAC name | Reference |
|---|---|---|
| D-1 | 4,4',4''-((1E,1'E,1''E)-cyclopropane-1,2,3-triylidenetris(cyanomethanylylidene))tris(2,3,5,6-tetrafluorobenzonitrile) [CAS 1224447-88-4] | US2008265216 |
| HOST-1 | H09 (Fluorescent-blue host material) | Commercially available from Sun Fine Chemicals, Inc, S. Korea |
| EMITTER-1 | BD200 (Fluorescent-blue emitter material) | Commercially available from Sun Fine Chemicals, Inc, S. Korea |
| ET-1 | 2,4-diphenyl-6-(4',5',6'-triphenyl-[1,1':2',1'':3'',1''':3''',1''''-quinquephenyl]-3''''-yl)-1,3,5-triazine [CAS 2032364-64-8] | WO2016171358 |
| Comparative-1 | 2,4-diphenyl-6-(3'-(9-phenyl-9H-fluoren-9-yl)-[1,1'-biphenyl]-4-yl)-1,3,5-triazine [CAS 2129116-80-7] | US0170250349 |
| LiQ | 8-Hydroxyquinolinolato-lithium [CAS 850918-68-2] | WO2013079217 |

To assess the performance of the inventive examples compared to the prior art, the current efficiency is measured at 20° C. The current-voltage characteristic is determined using a Keithley 2635 source measure unit, by sourcing a voltage in V and measuring the current in mA flowing through the device under test. The voltage applied to the device is varied in steps of 0.1V in the range between 0V and 10V. Likewise, the luminance-voltage characteristics and CIE coordinates are determined by measuring the luminance in $cd/m^2$ using an Instrument Systems CAS-140CT array spectrometer (calibrated by Deutsche Akkreditierungsstelle (DAkkS)) for each of the voltage values. The cd/A efficiency at 10 $mA/cm^2$ is determined by interpolating the luminance-voltage and current-voltage characteristics, respectively.

Lifetime LT of the device is measured at ambient conditions (20° C.) and 30 $mA/cm^2$, using a Keithley 2400 source meter, and recorded in hours.

The brightness of the device is measured using a calibrated photo diode. The lifetime LT is defined as the time till the brightness of the device is reduced to 97% of its initial value.

Properties of compounds A-1, A-2, A-3 and A-4 of formula (I) and of comparative-1 compound are shown in table 2 below.

TABLE 2
| Properties of compounds of formula (I) and of comparative compound Comparative-1 | | mp [° C.] | Tg [° C.] | $T_{RO}$ [° C.] |
|---|---|---|---|---|
| Comparative-1 | 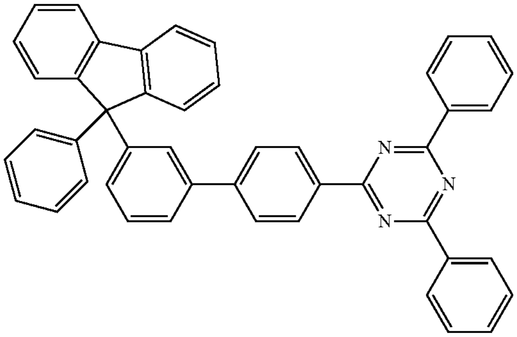 [SMILES: c1ccc(-c2nc(-c3ccccc3)nc(-c3ccc(-c4cccc(C5(c6ccccc6)c6ccccc6-c6ccccc65)c4)cc3)n2)cc1] | 303 | 123 | 268 |
| A-1 | 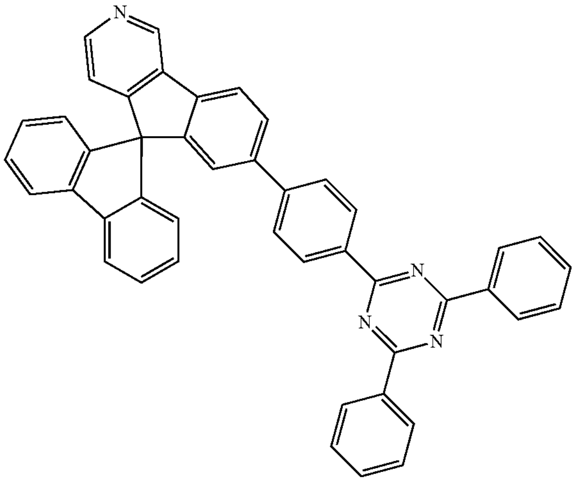 [SMILES: c1ccc(-c2nc(-c3ccccc3)nc(-c3ccc(-c4ccc5c(c4)C4(c6ccccc6-c6ccccc64)c4ccncc4-5)cc3)n2)cc1] | 299 | 155 | 240 |
| A-2 | 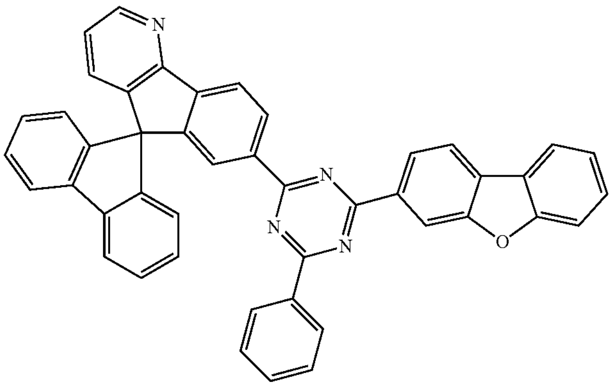 [SMILES: c1ccc(-c2nc(-c3ccc4c(c3)C3(c5ccccc5-c5ccccc53)c3cccnc3-4)nc(-c3ccc4c(c3)oc3ccccc34)n2)cc1] | 382 | 159 | 272 |

TABLE 2-continued

| Properties of compounds of formula (I) and of comparative compound Comparative-1 | | mp [° C.] | Tg [° C.] | $T_{RO}$ [° C.] |
|---|---|---|---|---|
| A-3 | 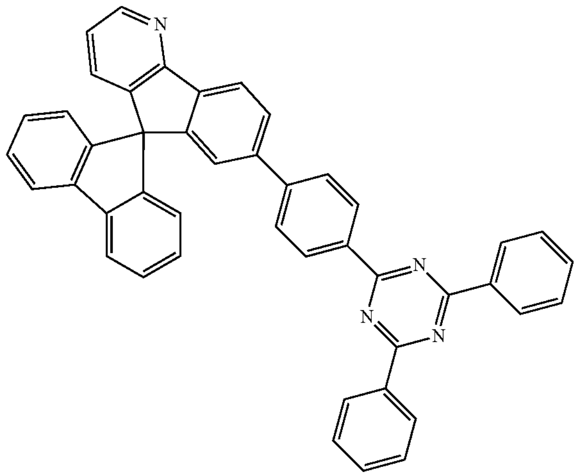 [SMILES: c1ccc(-c2nc(-c3ccccc3)nc(-c3ccc(-c4ccc5c(c4)C4(c6ccccc6-c6ccccc64)c4cccnc4-5)cc3)n2)cc1] | 298 | 154 | 252 |
| A-4 | 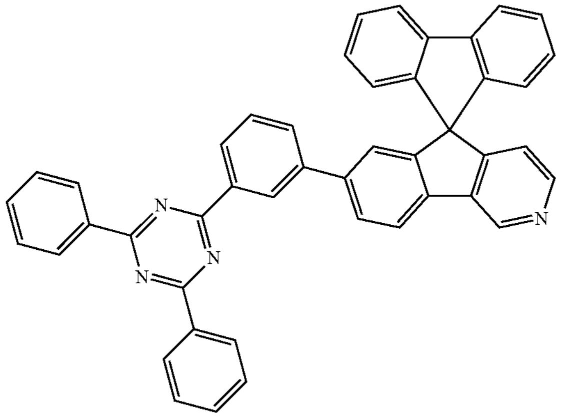 [SMILES: c1ccc(-c2nc(-c3ccccc3)nc(-c3cccc(-c4ccc5c(c4)C4(c6ccccc6-c6ccccc64)c4ccncc4-5)c3)n2)cc1] | 356 | 145 | 264 |

Dipole moment, HOMO and LUMO levels of comparative-1 and compounds A-1 to A-4, simulated by DFT (B3LYP_Gaussian/6-31G*, gas phase) are shown in table 3 below.

TABLE 3

Dipole moment, HOMO and LUMO levels of comapartive-1 and compounds A1 to A4, simulated by DFT (B3LYP_Gaussian/6-31G*, gas phase)

| | Dipole moment [Debye] | HOMO [eV] | LUMO [eV] |
|---|---|---|---|
| Comparative-1 | 0.58 | −5.81 | −1.85 |
| A-1 | 2.49 | −5.82 | −1.97 |
| A-2 | 1.54 | −5.83 | −2.01 |

TABLE 3-continued

Dipole moment, HOMO and LUMO levels of comapartive-1 and compounds A1 to A4, simulated by DFT (B3LYP_Gaussian/6-31G*, gas phase)

| | Dipole moment [Debye] | HOMO [eV] | LUMO [eV] |
|---|---|---|---|
| A-3 | 2.15 | −5.74 | −1.93 |
| A-4 | 2.60 | −5.81 | −1.83 |

The Performance data of an organic electroluminescent device comprising an organic semiconductor layer comprising compounds of formula 1, namely A-1 to A-3 as matrix material and an LiQ alkali organic complex in the electron transport layer are shown in table 4 below.

TABLE 4

Performance data of organic electroluminescent device comprising an organic semiconductor layer comprising compound of formula 1 as matrix material and an alkali organic complex in the electron transport layer

| OLED device examples | Matrix material | n-additive | Operating voltage at 10 mA/cm$^2$ (V) | LT97 at 30 mA/cm$^2$ (hours) |
|---|---|---|---|---|
| Comparative example | Comparative-1 | LiQ | 3.65 | 32 |
| Example-1 | A-1 | LiQ | 3.65 | 56 |
| Example-2 | A-2 | LiQ | 3.64 | 76 |
| Example-3 | A-3 | LiQ | 3.50 | 70 |

In summary, improved lifetime may be achieved when the organic semiconductor layer comprises a compound of formula 1, for example A-1 to A-3 and an organic metal complex, such as LiQ, compared with the prior art compound (comparative-1).

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. An organic light emitting diode (OLED) having a layer structure comprising, in order, the following layers: an anode layer, a hole injection layer, optionally a first hole transport layer, optionally a second hole transport layer, an emission layer, an electron transport layer, an electron injection layer, and a cathode layer, wherein the electron transport layer comprises a compound having formula A or formula B:

formula A

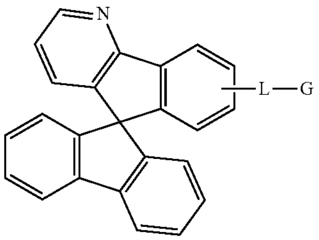

formula B

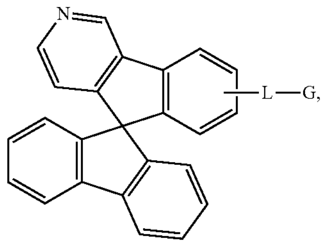

wherein L is a direct bond or phenylene;

wherein G is substituted or unsubstituted triazine wherein the substituents of the substituted triazine are independently selected from CN, deuterium, $C_6$ to $C_{18}$ aryl, $C_3$ to $C_{20}$ heteroaryl, $C_1$ to $C_{16}$ alkyl, $C_1$ to $C_{16}$ alkoxy, nitrile, or PY $(R^2)_2$ with Y being O or S;

and wherein $R^2$ are the same or different and independently selected from the group and wherein $R^2$ consisting of $C_1$ to $C_{16}$ alkyl, $C_1$ to $C_{16}$ alkoxy, $C_6$ to $C_{26}$ alkenyl, Co to $C_{18}$ aryl and $C_3$ to $C_{25}$ heteroaryl.

2. The OLED according to claim 1, wherein L is phenylene.

3. The OLED according to claim 1, wherein G is substituted triazine.

4. The OLED according to claim 1, wherein G is selected from D42 or D43:

(D42)

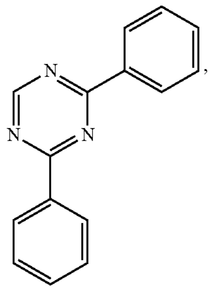

(D43)

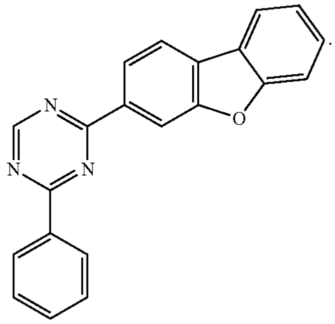

5. The OLED according to claim 1, wherein L is independently selected from F1 or F2:

(F1)

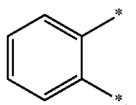

(F2)

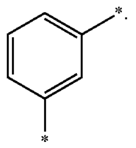

6. The OLED according to claim 1, wherein the compound is selected from G5, G6, G7, or G8:
(G5)
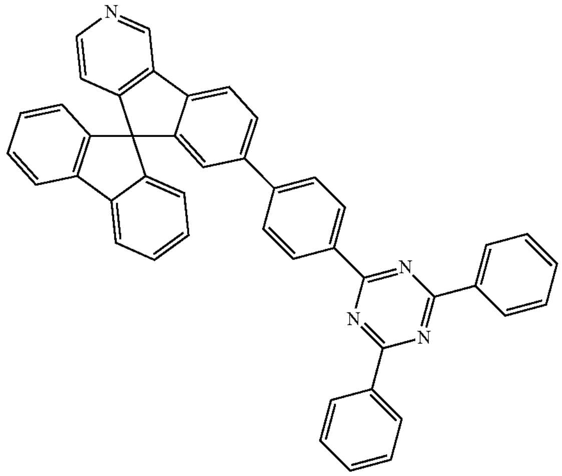
,
(G6)
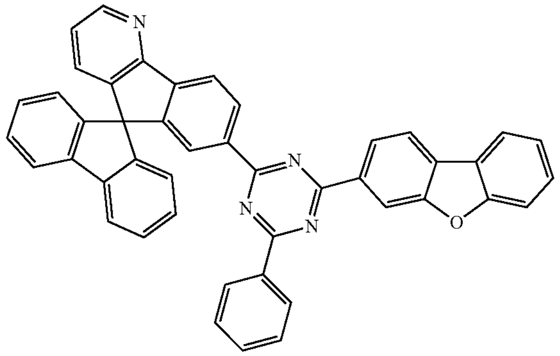
,
(G7)
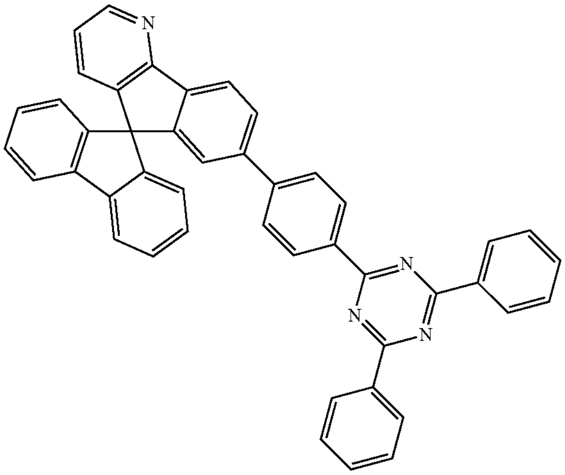
,
-continued
(G8)
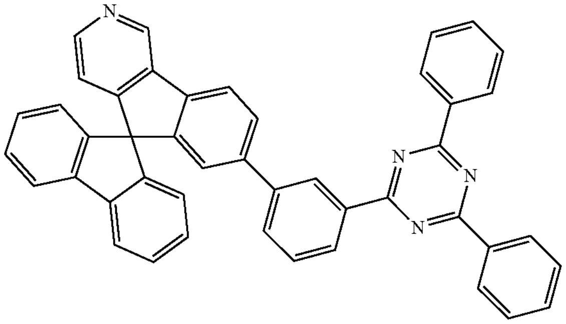
.
7. The OLED according to claim 1, wherein the OLED is a lighting device or a display device.
8. The OLED according to claim 1, wherein L is F3:
(F3)
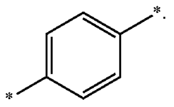
9. The OLED according to claim 1, wherein—
(i) L is selected from F1, F2, or F3—
(F1)
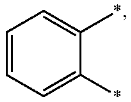
(F2)
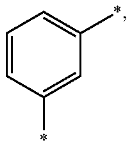
(F3)
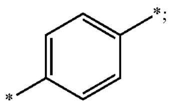

(ii) G is selected from D42 or D43—
(D42)
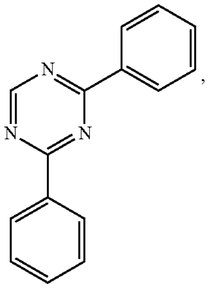
,
(D43)
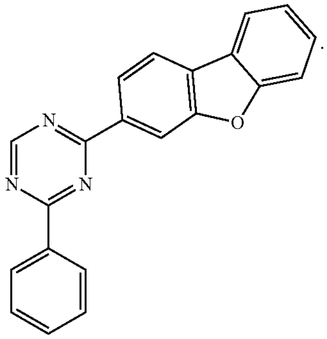
.
10. The OLED according to claim 1, wherein—
(i) L is the direct bond; and
(ii) G is selected from D42 or D43—
(D42)
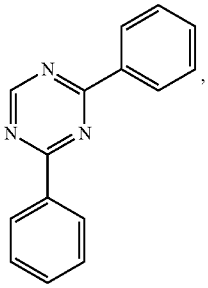
,
(D43)
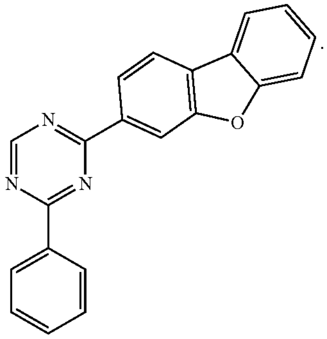
.
* * * * *